United States Patent [19]

Flaugh

[11] 4,081,458
[45] Mar. 28, 1978

[54] ANTI-ANDROGEN COMPOUNDS

[75] Inventor: Michael E. Flaugh, Indianapolis, Ind.

[73] Assignee: Eli Lilly and Company, Indianapolis, Ind.

[21] Appl. No.: 800,673

[22] Filed: May 26, 1977

[51] Int. Cl.$^2$ ............................................. C07D 493/04
[52] U.S. Cl. .................................... 260/335; 424/283
[58] Field of Search ........................................ 260/335

Primary Examiner—Norma S. Milestone
Attorney, Agent, or Firm—William C. Martens, Jr.; Arthur R. Whale

[57] ABSTRACT

Compounds of the formula

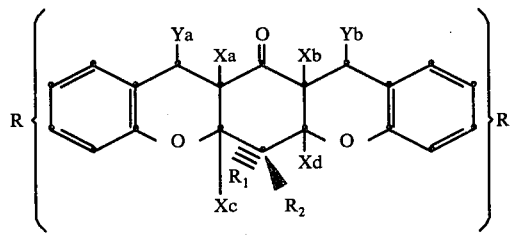

in which each R is hydrogen, $C_1$-$C_4$ alkyl, $C_1$-$C_4$ alkoxy, hydroxy, cyano, or halo, and both R groups are identical and are symmetrically located; $R_1$ is $C_1$-$C_3$ alkyl and $R_2$ is methyl, or $R_1$ and $R_2$ taken together are $-(CH_2)_n-$ in which $n$ is an integer from 4 to 6; and (1) $X_c$ and $X_d$ are hydrogen, and the combination of $X_a$ and $Y_a$ and of $X_b$ and $Y_b$ each represents a double bond, subject to the limitation that, when $R_1$ is $C_1$-$C_3$ alkyl and is other than methyl, $X_c$, $X_d$, and $R_1$ are all in an α-configuration; or (2) $X_a$, $X_b$, $X_c$, $X_d$, $Y_a$, and $Y_b$ are hydrogen, subject to the limitation that both $X_c$ and $X_d$ are in an α-configuration, both $X_a$ and $X_b$ are in an α-configuration or in a β-configuration, and, $R_1$, when it is $C_1$-$C_3$ alkyl, is in an α-configuration, are useful in inhibiting the action of androgens or are intermediates to such anti-androgen compounds.

35 Claims, No Drawings

ANTI-ANDROGEN COMPOUNDS

BACKGROUND OF THE INVENTION

This invention relates to a novel class of compounds having anti-androgen activity. Androgens are substances which are active in stimulating secondary sex characteristics in males. Although such substances obviously are of great physiological significance, they can produce certain undesirable side effects, and it would be highly advantageous to prophylactically or therapeutically eliminate or minimize these effects. For example, the stimulatory effects of androgens upon the prostate gland have been known for many decades. The pathogenesis of benign prostatic hypertrophy (BPH) and/or prostatic cancer (PC) is not fully understood; however, it is thought that both of these syndromes are subject to the influence of androgens. In addition, acne, an inflammatory disease involving the sebaceous glands and found chiefly in adolescents, is thought to be dependent upon sebum secretion which, in turn, is dependent upon androgen action. Other androgen-dependent conditions include hirsutism and certain types of cancer, including types of breast cancer.

Androgens are steroidal hormonal agents. For some time, it has been customary to attempt control of androgen activity by administration of other steroids. However, although administration of these steroids may be effective in diminishing androgen action, their administration in general results in other unwanted side effects which limit their usefulness. For example, cyproterone acetate is a potent steroidal anti-androgen. However, although it has demonstrated clinical effectiveness against both benign prostatic hypertrophy and prostatic cancer, it is not routinely used in humans because of its hormonal side effects. It has been reported to cause suppression of adrenal gland function as well as to exert potent progestational side effects.

It is highly desirable, therefore, to discover substances which are non-steroidal in structure and which exhibit potent anti-androgen activity. It is to such a class of compounds that this invention is directed. Only a very limited number of non-steroidal anti-androgens are recognized in the art. U.S. Pat. No. 3,857,953 discloses a class of arylidene cyclanones. These compounds are nonsteroidal, and they exhibit anti-androgen activity. It is to a new class of non-steroidal anti-androgens that this invention is directed.

SUMMARY OF THE INVENTION

As mentioned above, this invention relates to a class of compounds which are non-steroidal in structure and which exhibit potent androgen-inhibiting activity.

The compounds of this invention have the formula

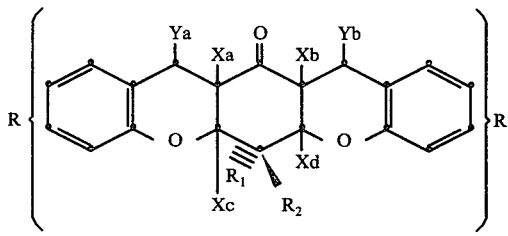

in which each R is hydrogen, $C_1$–$C_4$ alkyl, $C_1$–$C_4$ alkoxy, hydroxy, cyano, or halo, and both R groups are identical and are symmetrically located; $R_1$ is $C_1$–$C_3$ alkyl and $R_2$ is methyl or $R_1$ and $R_2$ taken together are $(CH_2)_n$ in which $n$ is an integer from 4 to 6; and (1) $X_c$ and $X_d$ are hydrogen, and the combination of $X_a$ and $Y_a$ and of $X_b$ and $Y_b$ each represents a double bond, subject to the limitation that, when $R_1$ is $C_1$–$C_3$ alkyl and is other than methyl, $X_c$, $X_d$, and $R_1$ are all in an α-configuration; or (2) $X_a$, $X_b$, $X_c$, $X_d$, $Y_a$, and $Y_b$ are hydrogen, subject to the limitation that both $X_c$ and $X_d$ are in an α-configuration, both $X_a$ and $X_b$ are in an α-configuration or in a α-configuration, and, $R_1$, when it is $C_1$–$C_3$ alkyl, is in an α-configuration.

DETAILED DESCRIPTION OF THE INVENTION

The compounds of this invention can be classified generally as dihydrobenzopyranoxanthenones and as hexahydrobenzopyranoxanthenones.

In all of the compounds of this invention, the carbon in the 6-position completes a $C_5$–$C_7$ spiro ring or is substituted both with a methyl ($R_2$) and with the group $R_1$ in which $R_1$ is $C_1$–$C_3$ alkyl. As used herein, the term "$C_1$–$C_3$ alkyl" refers to methyl, ethyl, n-propyl, or isopropyl. Preferably, $R_1$ is methyl, and when this is the case, a 6,6-dimethyl compound of course is defined. However, when $R_1$ is $C_1$–$C_3$ alkyl and is other than methyl, the substituents at the carbon in the 6-position are dissimilar, and, therefore, more than one isomer is possible. In those cases, the compounds of this invention are those in which the methyl group ($R_2$) is in a position generally axial to the ring while the group $R_1$ is in a position generally equatorial to the ring.

The dihydrobenzopyranoxanthenones of this invention have the general structure (I):

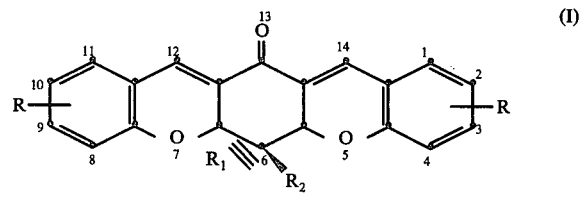

and the hexahydrobenzopyranoxanthenones have the general structure (II):

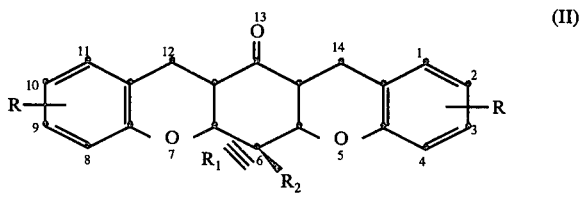

In the foregoing formulae I and II, the group R represents hydrogen, $C_1$–$C_4$ alkyl, $C_1$–$C_4$ alkoxy, hydroxy, cyano, or halo. As used herein, the term "$C_1$–$C_4$ alkyl" refers to methyl, ethyl, n-propyl, isopropyl, n-butyl, isobutyl, sec-butyl, and t-butyl. The term "$C_1$–$C_4$ alkoxy" as used herein refers to methoxy, ethoxy, n-propoxy, isopropoxy, n-butoxy, isobutoxy, sec-butoxy, and t-butoxy. As used herein, the term "halo" refers to chloro, fluoro, and bromo. Of the above groups, R preferably represents any of hydrogen, methoxy, ethoxy, or cyano.

In each of the compounds of this invention, the group R appears at two points. In any particular compound of this invention, the group R at both points in the molecule represents the same moiety. Furthermore, the groups designated as R, in any particular compound of this invention, are located symmetrically, and, thus, are at the 2- and 10-positions, the 3-and 9-positions, or the 4- and 8-positions.

In the dihydrobenzopyranoxanthenones of this invention, a hydrogen atom appears in both the 5a- and the 6a-positions. In order for the compound to exhibit anti-androgen activity, it is essential that the stereoconfiguration of these hydrogen atoms be such that they are cis to each other, that is, that both are located on the same side relative to the major plane of the molecule. In other words, both hydrogens must be in the α-position, or, what is equivalent, in the β-position.

The dihydrobenzopyranoxanthenones of this invention in which the 5a- and 6a-hydrogens are trans to each other, that is, those in which the 5a-hydrogen is in the α-position and the 6a-hydrogen is in the β-position, or vice versa, are not active as anti-androgens. However, they are readily epimerized to the active dihydrobenzopyranoxanthenones by simply warming them to a temperature moderately above room temperature. Therefore, these compounds are intermediates to the active dihydrobenzopyranoxanthenones.

The hexahydrobenzopyranoxanthenones of this invention differ from the dihydro compounds by hydrogenation of the double bonds at the 12- and 13a-carbons. The resulting hydrogenated products contain hydrogens at the 5a, 6a, 12, 12a, 13a, and 14-carbons. The particular stereoconfiguration of the hydrogens at the 5a, 6a, 12a, and 13a-carbons relative to each other is an essential factor in the definition of this invention. Of the various stereochemical combinations which are possible from these four hydrogens, two combinations represent compounds of this invention. The following two moieties of the hexahydrobenzopyranoxanthenones are included within the definition of this invention.

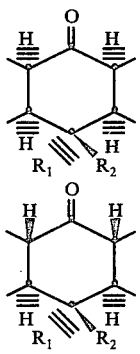

From the above, it is apparent that the hexahydrobenzopyranoxanthenones included within the definition of this invention comprise those in which (1) the hydrogens at the 5a- and the 6a-carbons are each cis to the other and (2) the hydrogens at the 12a- and the 13a-carbons are each cis to the other.

In addition to the above limitations pertaining to the stereoconfiguration of the compounds of this invention, a further limitation exists. The group $R_1$ can be a $C_1$–$C_3$ alkyl group. In those instances in which $R_1$ is methyl, a 6,6-dimethyl compound is defined, and no further stereoconfiguration considerations arise. However, when $R_1$ is other than methyl, a 6-methyl-6-ethyl, a 6-methyl-6-n-propyl, or a 6-methyl-6-isopropyl compound is defined. All of these represent compounds of this invention, however, the stereoconfigurational aspects are such that the compounds of this invention are restricted to those in which $R_1$ is in a position equatorial to the ring structure, and the methyl group ($R_2$) is in a position axial to the ring structure. In other words, the compounds of this invention in which $R_1$ is $C_1$–$C_3$ alkyl and is other than methyl are those in which the 5a and 6a hydrogens and the $R_1$ group are all in the α-position.

The dihydrobenzopyranoxanthenones of this invention are prepared by condensation of a 2-hydroxybenzaldehyde with a 4-methyl-4-alkyl-2,5-cyclohexadienone or a 4-cycloalkanespiro-2,5-cyclohexadienone in the presence of pyrrolidine and acetic acid. This reaction is depicted as follows:

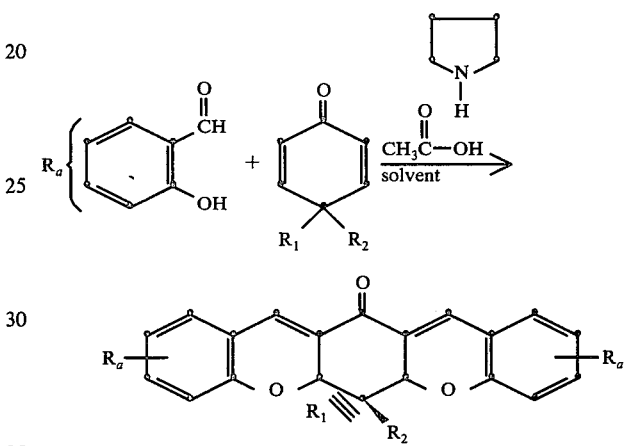

In the foregoing reaction, $R_a$ is hydrogen, $C_1$–$C_4$ alkyl, $C_1$–$C_4$ alkoxy, cyano, or halo. The reaction is carried out at a temperature of from about 0° C. to about 65° C. When the reaction is carried out at about room temperature or below, the product which results is predominantly a mixture of the 5aα, 6aβ- and the 5aβ, 6aα-optical isomers. These are useful intermediates and are compounds of this invention. This product, upon being subjected to a temperature above room temperature, rearranges to the 5aα, 6aα-isomer, a compound of this invention and a potent anti-androgen.

When the condensation of the 2-hydroxybenzaldehyde with a 4-substituted-2,5-cyclohexadienone is carried out at a temperature above room temperature, and generally from about 55° C. to about 65° C., the 5aα, 6aα-isomer product is isolated directly from the reaction mixture.

As is evident from the products obtained from the above reaction, at least a 2:1 molar ratio of the 2-hydroxybenzaldehyde to the 4-substituted-2,5-cyclohexadienone is required.

The condensation customarily can be carried out in any solvent which is inert to the reactants and which affords sufficient solubility for the reactants. In the event that epimerization affording direct isolation of the 5aα, 6aα-isomer is desired, the boiling point of the solvent must be high enough to achieve this result, that is, the boiling point must be in excess of about room temperature. Typical solvents which are employed include aromatic hydrocarbons, such as benzene, toluene, and the like, and ethers such as tetrahydrofuran, and the like. A proton source is employed, generally in an amount at least equivalent on a molar basis to the amount of the aldehyde which is employed. Typical proton sources include carboxylic acids such as acetic acid, propionic acid, butyric acid, and the like. The preferred acid is acetic acid. In addition, a secondary amine is employed, generally in an amount at least equivalent on a molar basis to the amount of carboxylic acid which is employed, and preferably in approximately a 10% molar excess relative to the carboxylic acid. Typical such secondary amines include, for example, pyrrolidine, piperidine, morpholine, and the like. The preferred secondary amine is pyrrolidine.

In carrying out the condensation, the reactants are mixed in the solvent of choice. The order of addition of the reactants is not critical; normally, however, the cyclohexadienone is added last. The mixture then is permitted to react at the selected temperature of reaction, and the product is recovered by customary techniques.

The starting materials employed in the condensation used to produce the dihydrobenzopyranoxanthenones of this invention are salicylaldehyde or a substituted salicylaldehyde and a 4-substituted-b 2,5-cyclohexadienone.

Salicylaldehyde as well as the 3-, 4-, or 5-substituted salicylaldehydes are available by techniques well recognized in the art. They, for example, can be prepared by the Reimer-Tiemann reaction which involves treatment of the appropriately substituted phenol with chloroform and an alkali metal hydroxide, particularly sodium hydroxide.

The dienone is available by either of two relatively complex reaction sequences which can be depicted as follows:

neat or in the presence of an inert solvent suitable for azeotropic removal of the water formed as by-product. Equimolar quantities of methyl vinyl ketone and the aldehyde or a moderate excess of up to about 10 percent of the aldehyde generally are employed. As indicated, the condensation preferably is carried out under acidic conditions. Although any of several strong acids can be used, sulfuric acid, methanesulfonic acid, benzenesulfonic acid, p-toluenesulfonic acid, and such like acids, are preferred. The condensation is exothermic, and, therefore, care must be exercised during the initial exothermic phase to avoid excessive temperature rise such as would cause polymerization of the methyl vinyl ketone.

Conversion of the 4-substituted-cyclohexenone to the desired product can be accomplished by either of two routes. The direct conversion (Route a) involves a dehydrogenation using dichlorodicyanoquinone (DDQ) in accordance with the literature procedure of H. E. Zimmerman et al., *J. Am. Chem. Soc.*, 93, 3653 (1971). Alternatively, the conversion can be achieved indirectly (Route b) by the sequence described in H. Plieninger et al., *Chem. Ber.*, 94, 2115 (1961). This sequence involves treating the 4-substituted-cyclohexenone with propen-2-yl acetate under acidic conditions to produce a 2-acetoxy-5-substituted-1,3-cyclohexadiene. The latter is treated with N-bromosuccinimide to produce a 4-substituted-6-bromocyclohex-2-enone which then is dehydrobrominated to the desired cyclohexadienone using hexamethylphosphoric triamide (HMPT). The use of HMPT is documented in Fieser and Fieser, *Reagents for Organic Synthesis*, Volume II, John Wiley and Sons, Inc., New York, 1969, pp. 209–210.

The compounds of this invention in which the group

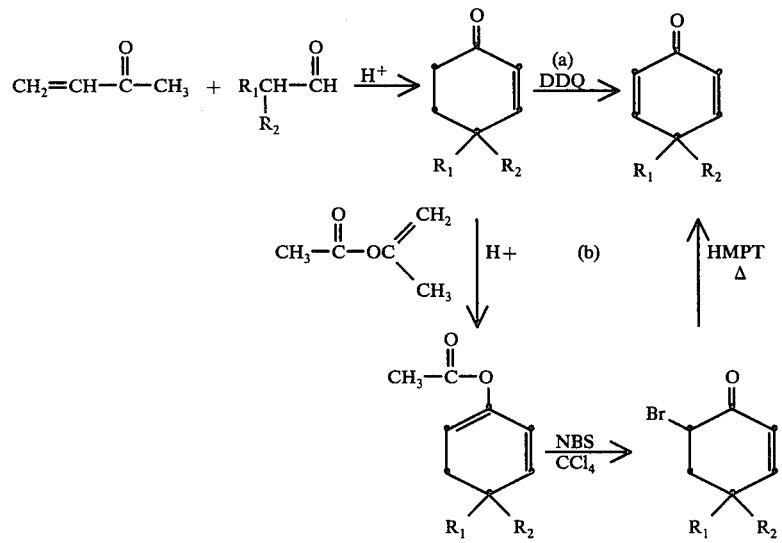

The formation of 4-substituted-cyclohexenones from methyl vinyl ketone and the appropriate aldehyde is well known from E. L. Eliel and C. Lukach, *J. Am. Chem. Soc.*, 79, 5986 (1957) and from Y. Chan and W. W. Epstein, *Org. Syn.*, 53, 48 (1973). It further has been discovered that this method is improved when carried out in acidic instead of alkaline conditions and in a manner analogous to that described for cyclic ketones by C. H. Heathcock et al., *Tetrahedron Letters*, 4995 (1971).

The condensation of methyl vinyl ketone with the aldehyde is readily controlled and may be carried out R is hydroxy are prepared by demethylation of the corresponding compounds in which R is methoxy. Demethylation is accomplished by treating the dimethoxy compound with boron tribromide. Typically, three molar equivalents of boron tribromide are added to a mixture of the dimethoxy compound in an inert solvent. The addition is carried out as rapidly as possible while retaining the temperature of the reaction mixture at about 0° C. Upon completion of the addition, the mixture is allowed to warm to room temperature and is maintained at room temperature for about 4 to about 16 hours. The product is recovered by adding the mixture to ice water and extracting the product into an appropriate solvent, such as, for example, methylene chloride, ethyl acetate, and the like.

The compounds of this invention in which R is alkoxy are also available from those compounds in which R is hydroxy. The hydroxy compounds are treated with a large excess of potassium carbonate and the appropriate alkyl bromide in the presence of hexamethylphosphoric triamide (HMPT) which itself can serve as solvent. The reaction is carried out at a elevated temperature of from about 50° C. to about 100° C. for from about 1 hour to about 20 hours.

The hexahydrobenzopyranoxanthenones of this invention are prepared by reduction of the dihydrobenzopyranoxanthenones. The reduction can be accomplished catalytically. For example, it can be carried out in an appropriate solvent over catalysts such as Raney nickel, palladium on carbon, platinum oxide, platinum on carbon, and the like. The reduction generally is carried out at room temperature or at a moderately elevated temperature of about 25° C. to about 50° C. and at a pressure of about 30 to about 60 p.s.i. The catalytic reduction usually is complete after about 4 to about 48 hours, and, more likely, after about 24 hours. The reduction can be carried out at atmospheric pressure; however, the reaction time thereby is greatly extended.

The reduction is carried out in the presence of a solvent. Typical solvents include ethers, such as tetrahydrofuran, and the like; esters, such as ethyl acetate, and the like; aromatic hydrocarbons, such as benzene, toluene, and the like; and alcohols, such as methanol, ethanol, and the like. An ether, especially tetrahydrofuran, is highly preferred as solvent.

The amount of catalyst which is employed ranges generally from about 10% to about 100% on a weight basis relative to the dihydrobenzopyranoxanthenone. In general, relative to each other, the amount of Raney nickel which is used greater than that of a platinum or palladium catalyst.

The reduction may produce a mixture of epimeric ketones. Although the positions of the hydrogens added to the 12a- and 13a-positions are cis to each other, they may be both α and β relative to the hydrogens located in the 5a- and 6a-positions. When Raney nickel or palladium are employed, approximately an 80:20 mixture of the epimers is obtained, the 12aα, 13aα isomer predominating. When platinum is used as catalyst, the product is virtually entirely the 12aα, 13aα isomer.

The catalytic reduction tends to be accompanied at least in part by reduction of the keto group in the 13-position, producing the corresponding hydroxyl compound. Thus, varying amounts of the corresponding alcohol are obtained. The Raney nickel and palladium catalysts produce about 30-50% over-reduction. Over-reduction is greater with a platinum catalyst and is virtually complete with an unsupported platinum catalyst.

The alcohol portion of the product mixture is back-oxidized to the desired hexahydro product by treatment with at least one equivalent of pyridinium chlorochromate, sodium dichromate, or potassium dichromate. It is preferred that the alcohol be isolated prior to back-oxidation; however, this is not essential, and the product mixture itself can be treated under oxidizing conditions. The oxidation is carried out at about room temperature in a solvent, such as methylene chloride or any of the aforedescribed solvents. When pyridinium chlorochromate is used, the oxidation is complete after about 24 hours. It is faster using a dichromate, being complete after about 1-4 hours.

The dihydrobenzopyranoxanthenones also can be converted to their corresponding hexahydrobenzopyranoxanthenones by electrolytic reduction. This method is sufficiently selective so that none of the aforedescribed over-reduction occurs.

The electrolytic reduction is carried out by dissolving or suspending the dihydrobenzopyranoxanthenone in an organic medium or in a medium comprising an aqueous-organic mixture. The aqueous-organic mixture itself can be present as an emulsion or as a miscible combination. Typical useful organic media include amides, such as N,N-dimethylformamide, N,N-dimethylacetamide, and the like; nitriles, such as acetonitrile, and the like; alcohols, such as methanol, ethanol, and the like; aromatic hydrocarbons, such as benzene, toluene, and the like; halogenated hydrocarbons, such as methylene chloride, chloroform, and the like; and such other organic media. Organic media which are preferred for use in the electrolysis process of this invention are amides, nitriles, and alcohols. Specifically preferred media include N,N-dimethylformamide, acetonitrile, and methanol. An especially preferred organic medium is methanol.

In addition, an electrolyte is added to the mixture. Useful electrolytes are salts such as halides, tosylates, perchlorates, and the like, of the alkali metals, such as lithium, sodium, and potassium. Other useful electrolytes are quaternary ammonium salts, such as halides, perchlorates, and the like. These include tetraalkylammonium, trialkylaralkylammonium, dialkyldiaralkylammonium, or alkyltriaralkylammonium, any of which have a total of about 10 to about 28 carbon atoms in the cation moiety. A preferred such salt is the tetrabutylammonium salt. A further class of electrolytes are tertiary amine salts, and these include halides, tosylates, perchlorates, and the like, of trialkylamines, dialkylaralkylamines, alkyldiaralkylamines, and triaralkylamines, any of which have a total of from about 7 to about 21 carbon atoms in the cation moiety. A preferred tertiary amine salt is a salt of tributylamine, and in particular, p-toluenesulfonic acid salt.

Examples of typical electrolytes include lithium perchlorate, potassium perchlorate, sodium perchlorate, lithium chloride, potassium bromide, sodium fluoride, sodium iodide, lithium iodide, tricaprylylmethylammonium chloride, benzyltributylammonium chloride, benzyltriethylammonium bromide, benzyltriethylammonium chloride, benzyltrimethylammonium bromide, cetyltrimethylammonium bromide, methyltributylammonium iodide, myristyltrimethylammonium bromide, tetrabutylammonium bromide, tetrabutylammonium chloride, tetrabutylammonium iodide, dibenzyldiethylammonium chloride, dibenzyldipropylammonium bromide, phenethyltributylammonium chloride, diphenethyldipentylammonium bromide, tribenzylethylammonium chloride, tetrahexylammonium chloride, triheptylbenzylammonium bromide, tripropylphenethylammonium iodide, tributylphenethylammonium chloride, N,N-diisopropyl-N-ethylamine perchlorate, tri-n-hexylamine bromide, N-benzyl-N,N-diethylamine p-toluenesulfonate, N-benzyl-N,N-dibutylamine bromide, N,N-dibenzyl-N-butylamine perchlorate, N,N-dibenzyl-N-ethylamine chloride, tribenzylamine p-toluenesulfonate, tributylamine chloride, and the like.

Furthermore, a source of protons is included in the reaction medium. This is found to expedite the electrolytic reduction defined by the process of this invention. Relatively weak acids having $pK_a$ values of from about 2 to about 6, such as benzoic acid, acetic acid, and the like, produce best results. Weaker acids, such as water, phenol, and the like, provide relatively poorer results, perhaps due to insufficient hydrogen ion activity. Strong acids, such as sulfuric acid, produced a hydrogen discharge at a potential lower than that required to effect the desired reduction, thereby preventing formation of the desired product.

As previously indicated, the dihydrobenzopyranoxanthenone substrate is reduced in an appropriate organic medium and in the presence of a selected electrolyte. In general, the substrate is present in an amount of from about 1 to about 15 mg. per ml. of medium. The electrolyte, in general, is present in an amount of from about 0.01 M to about 1.0 M, and, generally, the acid is present in an amount of about 1–5% by weight based upon the volume of the medium. The electrolytic reduction, in general, is carried out at a temperature of from about 5° C. to about 80° C., and, conveniently at about 20° C. to about 30° C.

The resulting mixture, containing the dihydrobenzopyranoxanthenone substrate, proton source, electrolyte, and organic or organic-aqueous medium, is placed in contact with the cathode of an electrolytic cell. A potential corresponding to a point at the foot of background discharge is applied. The potential is determined by preparing a current vs. potential curve at the working electrode on the medium prior to electrolysis. Current at the determined potential then is allowed to pass through the cell until an amount of current corresponding to between one and two times the number of Faradays required for a four-electron reduction has passed. The electrolysis is an especially convenient cathode reduction process which occurs with ease in commonly constructed electrolysis apparatus. The cathode is mercury. Anodic materials which can be used include platinum and carbon. Platinum metal is a preferred anode and particularly when it is in the form of a fine gauze or a wire mesh. Carbon, due to its low cost, represents another preferred anode.

The bridge connecting the cathode and anode can be a conventional salt bridge such as, for example, a 4 percent aqueous mixture saturated with potassium chloride. It can also be a suitable porous membrane such as, for example, an ion-exchange membrane, a ceramic membrane, or a sintered glass membrane of small to medium porosity.

A typical electrolytic cell comprises a jacketed glass cylindrical cathode compartment in which a glass anode compartment, part of which is a glass frit, is suspended. In general, the cathode is present as a ring-shaped pool of mercury. The anode compartment generally is a fritted glass cylinder or a circular double-walled glass tube having a circular glass frit sealed into its lower end. In general, the anode comprises a platinum wire immersed in the same mixture of the organic or organic-aqueous medium and electrolyte as is used in the cathode compartment. Normally, the electrolysis cell is stoppered with a cap through which a deaerating frit, a reference probe, and a thermometer are inserted. The reference electrode probe comprises a glass tube containing a fiber-junction in which a saturated calomel electrode is inserted.

In practice, the appropriate mixture containing the organic or organic-aqueous medium, electrolyte, and proton donor, is placed into the cathode compartment. A predetermined quantity (about 1–15 mg./ml.) of the dihydro-benzopyranoxanethenone is added to the stirred mixture, and the circular anode compartment containing the mixture of organic or organic-aqueous medium and electrolyte together with the electrolysis cell cap is properly positioned relative to the cathode. Argon then is introduced through the deaerating frit and into the stirred cathode mixture. Upon completion of deaeration (about 15 minutes), the deaerating frit is raised to a position above the surface of the cathode solution, and the flow of argon is continued throughout the electrolysis. A predetermined potential then is applied to the cell until an amount of current has passed which corresponds to approximately twice the number of Faradays required for a four electron reduction. Calculation of the coulombs which have passed through the system can be determined by means of a coulometer, and the system can also be monitored by means of thin-layer chromatography or high pressure liquid chromatography. Any of these methods are useful in determining the extend of reaction. Upon completion of the electrolysis, the catholyte solution is collected.

Workup of the reaction mixture is accomplished by routine techniques. In general, the majority of the organic or aqueous-organic medium first is removed in vacuo. The resulting syrupy residue then is dissolved in ethyl acetate. The ethyl acetate solution is washed several times with generally equal volume amounts of water to remove electrolyte as well as any proton donor which may have been employed. The ethyl acetate phase then is dried over a suitable drying agent, such as anhydrous magnesium sulfate, and is filtered. The ethyl acetate solvent is removed, and the residue is dried for several hours in a vacuum oven at about 45° C. The desired hexahydrobenzopyranoxanthenone product then is obtained by crystallization of the residue from an appropriate solvent system.

The cation of the electrolyte is a highly significant factor in the electrolysis reaction. It has been discovered that the stereoconfiguration of the hexahydrobenzopyranoxanthenone which is formed is to a great degree dependent upon the particular electrolyte which is used. When the electrolyte is a salt having a cation which forms a strongly associated ion pair, such as a lithium, sodium, or potassium cation, a product comprising predominantly the hexahydrobenzopyranoxanthenone having a $5a\alpha$, $6a\alpha$, $1a\alpha\beta$, $13a\beta$ configuration results. Conversely, an electrolyte having a cation which forms a weak ion pair, such as a quaternary ammonium salt or a tertiary amine salt, directs the electrolytic reduction to a product comprising predominantly the hexahydrobenzopyranoxanthenone having a $5a\alpha$, $6a\alpha$, $12a\alpha$, $13a\alpha$ configuration. Since, in general, the $\alpha,\alpha,\alpha,\alpha$-isomer is more active as an anti-androgen than is its $\alpha,\alpha,\beta,\beta$-isomer counterpart, it is highly preferred to employ a quaternary ammonium salt or a tertiary amine salt as electrolyte.

Examples of dihydrobenzopyranoxanthenones of this invention which are useful as intermediates in the preparation of anti-androgens are ($5a\alpha,6a\beta$)-6,6a-dihydro-6,6-dimethyl-5aH, 13H-(1)benzopyrano(3,2-b)xanthen-13-one;

($5a\alpha,6a\beta$)-6,6a-dihydro-4,8-dimethyl-6,6-dimethyl-5aH,13H-(1)benzopyrano(3,2-b)xanthen-13-one;

(5aα,6aβ)-6,6a-dihydro-3,9-diethyl-6,6-dimethyl-5aH,13H-(1)benzopyrano(3,2-b)xanthen-13-one;

(5aα,6aβ)-6,6a-dihydro-2,10-di-n-propyl-6,6-dimethyl-5aH,13H-(1)-benzopyrano(3,2-b)xanthen-13-one;

(5aα,6aβ)-6,6a-dihydro-2,10-di-t-butyl-6,6-dimethyl-5aH,13H-(1)benzopyrano(3,2-b)xanthen-13-one;

(5aα,6aβ)-6,6a-dihydro-3,9-dimethoxy-6,6-dimethyl-5aH,13H-(1)benzopyrano(3,2-b)xanthen-13-one;

(5aα,6aβ)-6,6a-dihydro-4,8-diethoxy-6,6-dimethyl-5aH,13H-(1)benzopyrano(3,2-b)xanthen-13-one;

(5aα,6aβ)-6,6a-dihydro-4,8-diisopropoxy-6,6-dimethyl-5aH,13H-(1)benzopyrano(3,2-b)xanthen-13-one;

(5aα,6aβ)-6,6a-dihydro-3,9-di-n-butoxy-6,6-dimethyl-5aH,13H-(1)benzopyrano(3,2-b)xanthen-13-one;

(5aα,6aβ)-6,6a-dihydro-4,8-dihydroxy-6,6-dimethyl-5-aH,13H-(1)benzopyrano(3,2-b)xanthen-13-one;

(5aα,6aβ)-6,6a-dihydro-3,9-dicyano-6,6-dimethyl-5aH,13H-(1)benzopyrano(3,2-b)xanthen-13-one;

(5aα,6aβ)-6,6a-dihydro-4,8-dichloro-6,6-dimethyl-5aH,13H-(1)benzopyrano(3,2-b)xanthen-13-one;

(5aα,6aβ)-6,6a-dihydro-4,8-difluoro-6,6-dimethyl-5aH,13H-(1)benzopyrano(3,2-b)xanthen-13-one;

(5aα,6aβ)-6,6a-dihydro-2,10-dibromo-6,6-dimethyl-5aH,13H-(1)benzopyrano(3,2-b)xanthen-13-one;

(5aα,6aβ)-6,6a-dihydrospiro[5aH, 13H-(1)benzopyrano(3,2-b)xanthene-6,1'-cyclopentan]-13-one;

(5aα,6aβ)-6,6a-dihydro-4,8-dimethylspiro[5aH,13H-(1)benzopyrano(3,2-b)xanthene-6,1'-cyclohexan]-13-one;

(5aα,6aβ)-6,6a-dihydro-3,9-diethylspiro[5aH,13H-(1)benzopyrano(3,2-b)xanthene-6,1'-cycloheptan]-13-one;

(5aα,6aβ)-6,6a-dihydro-2,10-di-n-propylspiro[5aH,13H-(1)benzopyrano(3,2-b)xanthene-6,1'-cyclopentan]-13-one;

(5aα,6aβ)-6,6a-dihydro-3,9-dimethoxyspiro[5aH,13H-(1)benzopyrano(3,2-b)xanthene-6,1'-cyclohexan]-13-one;

(5aα,6aβ)-6,6a-dihydro-4,8-diethoxyspiro[5aH,13H-(1)benzopyrano(3,2-b)xanthene-6,1'-cyclopentan]-13-one;

(5aα,6aβ)-6,6a-dihydro-4,8-dihydroxyspiro[5aH,13H-(1)benzopyrano(3,2-b)xanthene-6,1'-cyclohexan]-13-one; and the like.

Examples of dihydrobenzopyranoxanthenones of this invention which are useful as anti-androgens are (5aα,6aα)-6,6a-dihydro-6,6-dimethyl-5aH, 13H-(1)benzopyrano(3,2-b)xanthen-13-one;

(5aα,6aα)-6,6a-dihydro-6β-methyl-6α-ethyl-5aH,13H-(1)-benzopyrano(3,2-b)xanthen-13-one;

(5aα,6aα)-6,6a-dihydro-6β-methyl-6α-n-propyl-5aH,13H-(1)benzopyrano(3,2-b)xanthen-13-one;

(5aα,6aα)-6,6a-dihydro-6β-methyl-6α-isopropyl-5aH,13H-(1)benzopyrano(3,2-b)xanthen-13-one;

(5aα,6aα)-6,6a-dihydro-4,8-dimethyl-6,6-dimethyl-5aH,13H-(1)benzopyrano(3,2-b)xanthen-13-one;

(5aα,6aα)-6,6a-dihydro-3,9-diethyl-6,6-dimethyl-5aH,13H-(1)benzopyrano(3,2-b)xanthen-13-one;

(5aα,6aα)-6,6a-dihydro-2,10-di-n-propyl-6,6-dimethyl-5aH,13H-(1)benzopyrano(3,2-b)xanthen-13-one;

(5aα,6aα)-6,6a-dihydro-2,10-di-t-butyl-6β-methyl-6α-ethyl-5aH,13H-(1)benzopyrano(3,2-b)xanthen-13-one;

(5aα,6aα)-6,6a-dihydro-3,9-dimethoxy-6,6-dimethyl-5aH,13H-(1)benzopyrano(3,2-b)xanthen-13-one;

(5aα,6aα)-6,6a-dihydro-4,8-diethoxy-6β-methyl-6α-isopropyl-5aH,13H-(1)benzopyrano(3,2-b)xanthen-13-one;

(5aα,6aα)-6,6a-dihydro-4,8-diisopyropxy-6,6-dimethyl-5aH,13H-(1)benzopyrano(3,2-b)xanthen-13-one;

(5aα,6aα)-6,6a-dihydro-3,9-di-n-butoxy-6β-methyl-6α-n-propyl-5aH,13H-(1)benzopyrano(3,2-b)xanthene-13-one;

(5aα,6aα)-6,6a-dihydro-4,8-dihydroxy-6,6-dimethyl-5aH,13H-(1)benzopyrano(3,2-b)xanthen-13-one;

(5aα,6aα)-6,6a-dihydro-3,9-dicyano-6β-methyl-6α-ethyl-5aH,13H-(1)benzopyrano(3,2-b)xanthen-13-one;

(5aα,6aα)-6,6a-dihydro-4,8-dichloro-6β-methyl-6α-isopropyl-5aH,13H-(1)benzopyrano(3,2-b)xanthen-13-one;

(5aα,6aα)-6,6a-dihydro-4,8-difluoro-6,6-dimethyl-5aH,13H-(1)benzopyrano(3,2-b)xanthen-13-one;

(5aα,6aα)-6,6a-dihydrospiro[5aH,13H-(1)benzopyrano(3,2-b)xanthene-6,1'-cyclohexan]-13-one;

(5aα, 6aα)-6,6a-dihydro-4,8-dimethylspiro[5aH,13H-(1)benzopyrano(3,2-b)xanthene-6,1'-cyclopentan]-13-one;

(5aα, 6aα)-6,6a-dihydro-3,9-diethylspiro[5aH,13H-(1)benzopyrano(3,2-b)xanthene-6,1'-cycloheptan]-13-one;

(5aα, 6aα)-6,6a-dihydro-3,9-dimethoxyspiro[5aH,13H-(1)benzopyrano(3,2-b)xanthene-6,1'-cyclohexan]-13-one;

(5aα, 6aα)-6,6a-dihydro-4,8-diethoxyspiro[5aH,13H-(1)benzopyrano(3,2-b)xanthene-6,1'-cyclopentan]-13-one;

(5aα, 6aα)-6,6a-dihydro-4,8-dihydroxyspiro[5aH,13H-(1)benzopyrano(3,2-b)xanthene-6,1'-cyclohexan]-13-one;

(5aα, 6aα)-6,6a-dihydro-2,10-dibromo-6,6-dimethyl-5aH,13H-(1)benzopyrano(3,2-b)xanthen-13-one; and the like.

Examples of hexahydrobenzopyranoxanthenones of this invention are (5aα, 6aα, 12aα, 13aα)-6,6a, 12,12a13a,14-hexahydro-6,6-dimethyl-5aH,13H-(1)benzopyrano(3,2-b)xanthen-13-one;

(5aα, 6aα, 12aα, 13aα)-6,6a,12,12a,13a,14-hexahydro-6β-methyl-6α-ethyl-5aH,13H-(1)benzopyrano(3,2-b)xanthen-13-one;

(5aα, 6aα, 12aα, 13aα)-6,6a,12,12a,13a,14-hexahydro-6β-methyl-6α-n-propyl-5aH,13H-(1)benzopyrano(3,2-b)xanthen-13-one;

(5aα, 6aα, 12aα, 13aα)-6,6a,12,12a,13a14-hexahydro-6β-methyl-6α-isopropyl-5aH,13H-(1)benzopyrano(3,2-b)xanthen-13-one;

(5aα, 6aα, 12aα, 13aα)-6,6a,12,12a,13a,14-hexahydro-4,8-dimethyl-6,6-dimethyl-5aH,13H-(1)benzopyrano(3,2-b)-xanthen-13-one;

(5aα, 6aα, 12aα, 13aα)-6,6a,12,12a,13a,14-hexahydro-3,9-diethyl-6,6-dimethyl-5aH,13H-(1)benzopyrano(3,2-b)-xanthen-13-one;

(5aα, 6aα,12aα, 13aα)-6,6a,12,12a,13a,14-hexahydro-2,10-di-n-propyl-6,6-dimethyl-5aH,13H-(1)benzopyrano(3,2-b)-xanthen-13-one;

(5aα, 6aα, 12aα, 13aα)-6,6a,12,12a,13a,14-hexahydro-2,10-di-t-butyl-6β-methyl-6α-ethyl-5aH,13H-(1)benzopyrano-(3,2-b)-xanthen-13-one;

(5aα, 6aα, 12aα, 13aα)-6,6a,12,12a,13a,14-hexahydro-3,9-dimethoxy-6,6-dimethyl-5aH,13H-(1)benzopyrano(3,2-b)xanthen-13-one;

(5aα, 6aα, 12aα, 13aα)-6,6a,12,12a,13a,14-hexahydro-4,8-diethoxy-6β-methyl-6α-ethyl-5aH,13H-(1)benzopyrano(3,2-b)xanthen-13-one;

(5aα, 6aα, 12aα, 13aα)-6,6a,12,12a,13a,14-hexahydro-4,8-diisopropoxy-6,6-dimethyl-5aH,13H-(1)benzopyrano-(3,2-b)xanthen-13-one;

(5aα, 6aα, 12aα, 13aα)-6,6a,12,12a,13a,14-hexahydro-3,9-di-n-butoxy-6β-methyl-6α-ispropyl-5aH,13H-(1)benzopyrano(3,2-b)xanthen-13-one;

(5aα, 6aα, 12aα, 13aα)-6,6a,12,12a,13a,14-hexahydro-4,8-dihydroxy-6,6-dimethyl-5aH,13H-(1)benzopyrano(3,2-b)xanthen-13-one;

(5aα, 6aα, 12aα, 13aα)-6,6a,12,12a,13a,14-hexahydro-3,9-dicyano-6β-methyl-6α-ethyl-5aH,13H-(1)benzopyrano(3,2-b)-xanthen-13-one;

(5aα, 6aα, 12aα, 13aα)-6,6a,12,12a,13a,14-hexahydro-4,8-dichloro-6β-methyl-6α-isopropyl-5aH,13H-(1)benzopyrano-(3,2-b)xanthen-13-one;

(5aα, 6aα, 12aα, 13aα)-6,6a,12,12a,13a,14-hexahydro-4,8-difluoro-6,6-dimethyl-5aH,13H-(1)benzopyrano(3,2-b)-xanthen-13-one;

(5aα, 6aα, 12aα, 13aα)-6,6a,12,12a,13a,14-hexahydro-2,10-dibromo-6,6-dimethyl-5aH,13H-(1)benzopyrano(3,2-b)-xanthen-13-one;

(5aα, 6aα, 12aβ, 13aβ)-6,6a,12,12a,13a, 14-hexahydro-6,6-dimethyl-5aH,13H-(1)benzopyrano(3,2-b)xanthen-13-one;

(5aα, 6aα, 12aβ, 13aβ)-6,6a12,12a,13a,14-hexahydro-6β-methyl-6α-ethyl-5aH,13H-(1)benzopyrano(3,2-b)xanthen-13-one;

(5aα, 6aα, 12aβ, 13aβ)-6,6a,12,12a,13a,14-hexahydro-6β-methyl-6α-n-propyl-5aH,13H-(1)benzopyrano(3,2-b)xanthen-13-one;

(5aα, 6aα, 12aβ, 13aβ)-6,6a,12,12a,13a,14-hexahydro-4,8-diethyl-6,6-dimethyl-5aH,13H-(1)benzopyrano(3,2-b)-xanthen-13-one;

(5aα, 6aα, 12aβ, 13aβ)-6,6a,12,12a,13a,14-hexahydro-4,8-dimethyl-6,6-dimethyl-5aH,13H-(1)benzopyrano(3,2-b)-xanthen-13-one;

(5aα, 6aα, 12aβ, 13aβ)-6,6a,12,12a,13a,14-hexahydro-3,9-diethyl-6,6-dimethyl-5aH,13H-(1)benzopyrano(3,2-b)-xanthen-13-one;

(5aα, 6aα, 12aβ, 13aβ)-6,6a,12,12a,13a,14-hexahydro-2,10-di-n-propyl-6,6-dimethyl-5aH,13H-(1)benzopyrano(3,2-b)xanthen-13-one;

(5aα, 6aα, 12aβ, 13aβ)-6,6a,12,12a,13a,14-hexahydro-2,10-di-t-butyl-6β-methyl-6α-ethyl-5aH,13H-(1)benzopyrano-(3,2-b)xanthen-13-one;

(5aα, 6aα, 12aβ, 13aβ)-6,6a,12,12a,13a,14-hexahydro-3,9-dimethoxy-6,6-dimethyl-5aH,13H-(1H)benzopyrano(3,2-b)-xanthen-13-one;

(5aα, 6aα, 12aβ, 13aβ)-6,6a,12,12a,13a,14-hexahydro-4,8-diethoxy-6β-methyl-6α-ethyl-5aH,13H-(1)benzopyrano(3,2-b)xanthen-13-one;

(5aα, 6aα, 12aβ, 13aβ)-6,6a,12,12a,13a,14-hexahydro-4,8-diisopropoxy-6,6-dimethyl-5aH,13H-(1)benzopyrano(3,2-b)xanthen-13-one;

(5aα, 6aα, 12aβ, 13aβ)-6,6a,12,12a,13a, 14-hexahydro-3,9-di-n-butoxy-6β-methyl-6α-isopropyl-5aH,13H-(1)benzopyrano(3,2-b)xanthen-13-one;

(5aα, 6aα, 12aβ, 13aβ)-6,6a,12,12a,13a,14-hexahydro-4,8-dihydroxy-6,6-dimethyl-5aH,13H-(1)benzopyrano(3,2-b)xanthen-13-one;

(5aα, 6aα, 12aβ, 13aβ)-6,6a,12,12a,13a,14-hexahydro-3,9-dicyano-6β-methyl-6α-ethyl-5aH,13H-(1)benzopyrano(3,2-b)xanthen-13-one;

(5aα, 6aα, 12aα, 13aα)-6,6a,12,12a,13a,14-hexahydrospiro[5aH,13H-(1)benzopyrano(3,2-b)xanthene-6,1'-cyclohexan]-13-one;

(5aα, 6aα, 12aα, 13aα)-6,6a,12,12a,13a,14-hexahydrospiro-[5aH,13H-(1)benzopyrano(3,2-b)xanthene-6,1'-cyclopentan]-13-one;

(5aα, 6aα, 12aα, 13aα)-6,6a,12,12a,13a,14-hexahydro-4,8-dimethylspiro[5aH,13H-(1)benzopyrano(3,2-b)xanthene-6,1'-cyclohexan]-13-one;

(5aα, 6aα, 12aα, 13aα)-6,6a,12,12a,13a,14-hexahydro-3,9-dimethoxyspiro[5aH,13H-(1)benzopyrano(3,2-b)xanthene-6,1'-cyclohexan]-13-one;

(5aα, 6aα, 12aα, 13aα)-6,6a,12,12a,13a,14-hexahydro-4,9-diethoxyspiro[5aH,13H-(1)benzopyrano(3,2-b)xanthene-6,1'-cycloheptan]-13-one;

(5aα, 6aα, 12aα, 13aα)-6,6a,12,12a,13a,14-hexahydro-4,8-dihydroxyspiro[5aH,13H-(1)benzopyrano(3,2-b)xanthene-6,1'-cyclohexan]-13-one;

(5aα, 6aα, 12aα, 13aα)-6,6a,12,12a,13a,14-hexahydro-4,8-dichlorospiro[5aH,13H-(1)benzopyrano(3,2-b)xanthene-6,1'-cyclopentan]-13-one;

(5aα, 6aα, 12aα, 13aα)-6,6a,12,12a,13a,14-hexahydro-2,10-dibromospiro[5aH,13H-(1)benzopyrano(3,2-b)xanthene-6,1'-cycloheptan]-13-one;

(5aα, 6aα, 12aβ, 13aβ)-6,6a,12,12a,13a,14-hexahydrospiro[5aH,13H-(1)benzopyrano(3,2-b)xanthene-6,1'-cyclopentan]-13-one;

(5aα, 6aα, 12aβ, 13aβ)-6,6a,12,12a,13a,14-hexahydrospiro[5aH,13H-(1)benzopyrano(3,2-b)xanthene-6,1'-cyclohexan]-13-one;

(5aα, 6aα, 12aβ, 13aβ)-6,6a,12,12a,13a,14-hexahydro-4,8-dimethylspiro[5aH,13H-(1)benzopyrano(3,2-b)xanthene-6,1'-cyclohexan]-13-one;

(5aα, 6aα, 12aβ, 13aβ)-6,6a,12,12a,13a,14-hexahydro-3,9-diethylspiro[5aH,13H-(1)benzopyrano(3,2-b)xanthene-6,1'-cycloheptan]-13-one;

(5aα,6aα,12aβ,13aβ)-6,6a,12,12a,13a,14-hexahydro-3,9-dimethoxyspiro[5aH,13H-(1H)benzopyrano(3,2-b)xanthene-6,1'-cyclopentan]-13-one;

(5aα,6aα,12aβ,13aβ)-6,6a,12,12a,13a,14-hexahydro-4,8-diethoxyspiro[5aH,13H-(1)benzopyrano(3,2-b)xanthene-6,1'-cyclohexan]-13-one;

(5aα,5aα,12aβ,13aβ)-6,6a,12,12a,13a,14-hexahydro-4,8-dihydroxyspiro[5aH,13H-(1)benzopyrano(3,2-b)xanthene-6,1'-cycloheptan]-13-one;

(5aα,6aα,12aβ,13aβ)-6,6a,12,12a,13a,14-hexahydro-3,9-dicyanospiro[5aH,13H-(1)benzopyrano(3,2-b)xanthene-6,1'-cyclopentan]-13-one;

(5aα,6aα,12aβ,13aβ)-6,6a,12,12a,13a,14-hexahydro-4,8-dichlorospiro[5aH,13H-(1)benzopyrano(3,2-b)xanthene-6,1'-cyclohexan]-13-one;

(5aα,6aα,12aβ,13aβ)-6,6a,12,12a,13a,14-hexahydro-4,8-dichloro-6β-methyl-6α-isopropyl-5aH,13H-(1)benzopyrano-(3,2-b)xanthen-13-one;

(5aα,6aα,12aβ,13aβ)-6,6a,12,12a,13a,14-hexahydro-4,8-difluoro-6,6-dimethyl-5aH,13H-(1)benzopyrano(3,2-b)xanthen-13-one.

(5aα,6aα,12aβ,13aβ)-6,6a,12,12a,13a,14-hexahydro-2,10-dibromo-6,6-dimethyl-5aH,13H-(1)benzopyrano(3,2-b)xanthen-13-one; and the like.

The 5aα,6aα-dihydropyranoxanthenones and the hexahydropyranoxanthenones of this invention possess the characteristics of exerting an anti-androgenic response when administered at a dose range from about 0.05 mg. to about 100 mg. per kg. body weight. They therefore are useful in treating or alleviating androgen-caused or androgen-dependent conditions such as benign prostatic hypertrophy, acne, prostatic cancer, and the like.

The compounds of this invention can be administered orally in the form of tablets, capsules, elixirs, and the like. They can also be administered by parenteral injection. In addition, they can be administered in the form of suppositories and lotions. In tablet form, they are compounded with an inert pharmaceutical carrier which may contain a suitable binder such as, for example, gums, starches, and sugars. They may also be incorporated into gelatin capsules or formulated into elixirs which have the advantage of being susceptable to flavoring by the addition of standard natural or synthetic flavoring agents. Administration may also be achieved in the form of aqueous parenteral suspensions. Compounds of this invention effectively produce an anti-androgenic effect at about 0.05 mg. to about 100 mg./kg body weight on a daily basis. Preferably, these formulations are so proportioned as to afford a unit dosage of from about 1 to about 500 mg. of active compound. Particularly preferred unit dosages are those ranging from about 50 to about 250 mg. Preferably, the compounds are administered orally.

The anti-androgen activity of the compounds of this invention is demonstrated by a standard in vivo rat assay utilizing castrate immature male rats. The assay is routinely conducted using immature male rats, usually 21 days old, which have been bi-laterally castrated and left untreated for three days. This provides adequate time for metabolism of endogenous androgens and for atrophy of the secondary sex organs to begin. The castrate rats then are divided into at least three treatment groups. Ten rats are injected subcutaneously once each day with 0.02 mg. of testosterone propionate (TP) suspended in corn oil. These rats serve as an androgen-stimulated control group. Another group of five rats is injected subcutaneously once each day with the corn oil vehicle, and these serve as a castrate control group. The third treatment group consists of five rats, each of which receive 0.02 mg. of TP subcutaneously and an experimental compound either orally or subcutaneously once eacy day. A separate experimental group is used for each compound and for each dose level tested. All animals are treated for seven consecutive days. On the eighth day, all rats, usually now 28 days old, are sacrificed and autopsied. At autopsy, the seminal vesicles (SV) and ventral prostate (VP) glands are removed and weighed.

The weights of the SV and VP of the castrate control group are subtracted from those of the androgen-stimulated group to determine the androgen stimulation resulting from exogenous TP administration. The SV and VP weights of each experimental group are substracted from those of the androgen-stimulated group, and the difference is divided by the increase in organ weight resulting from TP treatment alone. These differences are expressed as percent inhibition.

The effect of the administered compound upon the stimulatory effect of exogenous TP is evidenced by the failure of the weighed endocrine glands to increase in weight at the rate indicated for the TP stimulated rats which do not receive any of the experimental compound.

The Table following demonstrates the androgen-inhibiting activity of the compounds of this invention.

TABLE

Anti-Androgen Activity

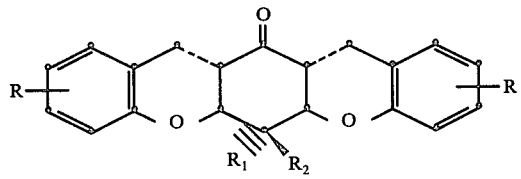

| Test Group[1] | R | $R_1$ | $R_2$ | Stereoconfiguration | Dose, mg/day[2] | Change, % VP | SV |
|---|---|---|---|---|---|---|---|
| 1 | H | $CH_3$ | $CH_3$ | Dihydro; 5α,6α | 0.03 (s.c.) | −62 | −75 |
| 1 | 2,10-Di—$OCH_3$ | $CH_3$ | $CH_3$ | Dihydro; 5α,6α | 0.03 (s.c.) | −68 | −64 |
| 1 | 3,9-Di—$OCH_3$ | $CH_3$ | $CH_3$ | Dihydro; 5α,6α | 0.03 (s.c.) | −71 | −82 |
| 1 | 4,8-Di—$OCH_3$ | $CH_3$ | $CH_3$ | Dihydro; 5α,6α | 0.03 (s.c.) | −69 | −70 |
| 1 | 4,8-Di—OH | $CH_3$ | $CH_3$ | Dihydro; 5α,6α | 0.10 (s.c.) | −45 | −56 |
| 1 | H | $CH_3$ | $CH_3$ | Hexahydro; 5α,6α,12α,13α | 0.03 (s.c.) | −80 | −86 |
| 1 | 2,10-Di—$OCH_3$ | $CH_3$ | $CH_3$ | Hexahydro[3] | 0.03 (s.c.) | −78 | −87 |
| 1 | 3,9-Di—$OCH_3$ | $CH_3$ | $CH_3$ | Hexahydro[3] | 0.03 (s.c.) | −83 | −73 |
| 1 | 4,8-Di—$OCH_3$ | $CH_3$ | $CH_3$ | Hexahydro; 5α,6α,12aβ,13aβ | 0.10 (s.c.) | −47 | −44 |
| 1 | 4,8-Di—OH | $CH_3$ | $CH_3$ | Hexahydro; 5α,6α,12α,13α | 0.10 (s.c.) | −26 | −50 |
| 1 | 4,8-Di—$OCH_3$ | $CH_3$ | $CH_3$ | Hexahydro; 5α,6α,12α,13α | 0.03 (s.c.) | −77 | −74 |
| 2 | 2,10-Di—$OCH_3$ | $CH_3$ | $CH_3$ | Hexahydro; 5α,6α,12α,13α | 0.03 (oral) | −14 | −17 |
| 2 | 3,9-Di—$OCH_3$ | $CH_3$ | $CH_3$ | Hexahydro; 5α,6α,12α,13α | 0.03 (oral) | −14 | −18 |
| 2 | 3,9-Di—$OCH_3$ | $CH_3$ | $CH_3$ | Hexahydro; 5α,6α,12aβ,13aβ | 0.03 (oral) | −20 | −18 |
| 2 | 4,8-Di—$OCH_3$ | $CH_3$ | $CH_3$ | Hexahydro; 5α,6α,12α,13aβ | 0.03 (oral) | +6 | +10 |
| 2 | 4,8-Di—$OCH_3$ | $CH_3$ | $CH_3$ | Hexahydro; 5α,6α,12α,13α | 0.03 (oral) | −49 | −40 |
| 3 | 4,8-Di—OH | $CH_3$ | $CH_3$ | Dihydro; 5α,6α | 0.03 (oral) | −54 | −63 |
| 3 | 4,8-Di—OH | $CH_3$ | $CH_3$ | Hexahydro; 5α,6α,12α,13α | 0.03 (oral) | −58 | −60 |
| 3 | 4,8-Di—$OCH_3$ | $CH_3$ | $CH_3$ | Hexahydro; 5α,6α,12α,13α | 0.03 (oral) | −56 | −49 |
| 4 | 4,8-Di—$OC_2H_5$ | $CH_3$ | $CH_3$ | Dihydro; 5α,6α | 0.03 (oral) | −45 | −55 |
| 4 | 4,8-Di—$OC_2H_5$ | $CH_3$ | $CH_3$ | Hexahydro; 5α,6α,12α,13α | 0.03 (oral) | −40 | −44 |
| 4 | 4,8-Di—$OCH_3$ | $CH_3$ | $CH_3$ | Hexahydro; 5α,6α,12α,13α | 0.03 (oral) | −49 | −50 |
| 5 | H | $C_2H_5$ | $CH_3$ | Dihydro; 5α,6α | 0.03 (oral) | −61 | −63 |
| 5 | H | $C_2H_5$ | $CH_3$ | Hexahydro; 5α,6α,12α,13α | 0.03 (oral) | −50 | −34 |
| 5 | 4,8-Di—$OCH_3$ | $C_2H_5$ | $CH_3$ | Dihydro; 5α,6α | 0.03 (oral) | −57 | −60 |
| 5 | 4,8-Di—$OCH_3$ | $C_2H_5$ | $CH_3$ | Hexahydro; 5α,6α,12α,13α | 0.03 (oral) | −66 | −63 |
| 5 | H | —$C_5H_{10}$— | | Dihydro; 5α,6α | 0.03 (oral) | −53 | −56 |
| 5 | H | —$C_5H_{10}$— | | Hexahydro; 5α,6α,12α,13α | 0.03 (oral) | −58 | −45 |

TABLE-continued

Anti-Androgen Activity

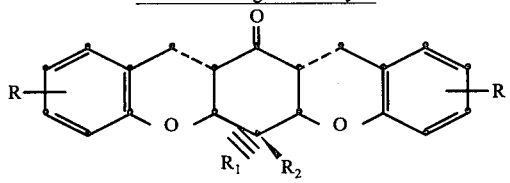

| Test Group[1] | R | $R_1$ | $R_2$ | Stereoconfiguration | Dose, mg/day[2] | Change, % VP | SV |
|---|---|---|---|---|---|---|---|
| 5 | 4,8-Di—$OCH_3$ | $CH_3$ | $CH_3$ | Hexahydro; 5aα,6aα,12aα,13aα | 0.03 (oral) | −72 | −71 |

Footnotes.
1. Designates those compounds tested during a particular run. Since the sensitivity of this assay varies from one run to another, the potency of a given compound should be compared to that of others in the same run. For this purpose, 6,6aα,12,12aα,13aα,14-hexahydro-4,8-dimethoxy-6,6-dimethyl-5aαH,13H-(1)benzopyrano(3,2-b)xanthan-13-one is employed as standard and appears in east test group.
s.c. — subcutaneous.
3. Mixture of Hexahydro epimers (a) 6aα,6aα,12aα,13aα and (b) 5aα,6aα,12aβ,13aβ.

The following are provided to illustrate preparations of compounds useful in preparing compounds of this invention.

Preparation A. 4,4-Dimethyl-2-cyclohexenone.

A mixture of 743 ml. (630 g. 8 moles) of freshly distilled methyl vinyl ketone and 1250 ml (940 g, 13.7 moles) of isobutyraldehyde was prepared in a 3 L. flask. Over a period of two minutes 9 ml. of conc. sulfuric acid were added to the mixture. The mixture was stirred magnetically and was cooled with an ice water bath to maintain an internal temperature of 45°-50° C. After one hour the bath was removed, and the mixture was refluxed through a Dean-Stark trap for three hours. The mixture then was distilled through a short Vigreaux column at 15 mm. pressure. The main fraction, $b_{15}$ 70°-77° C., was fairly pure product, possibly containing a small amount of isobutyraldehyde. Yield: 751 g (67%). Redistillation gave a sharper boiling product ($b_{15}$ 74°-79° C.), free of isobutyraldehyde.

Preparation B. 4,4-Dimethyl-2,5-cyclohexadienone.

Method a. Using 2,3-dichloro-5,6-dicyanobenzoquinone.

To 1.5 liters of toluene were added 134.9 g (1.1 moles) of 4,4-dimethyl-2-cyclohexenone and 249 g (1.21 moles) of 2,3-dichloro-4,5-dicyanobenzoquinone (DDQ). The resulting mixture was refluxed under nitrogen for 3.5 hours. During this time a precipitate of 2,3-dichloro-4,5-dicyanohydroquinone (DDH) was deposited from the initially dark red solution. The reaction mixture then was cooled, and the DDH was collected by filtration. A major portion of the toluene was removed by rotary evaporation, and the resulting residue was dissolved in ether. The ether solution was washed with 1N sodium hydroxide several times until the washings were clear and then was washed with water. After drying, the ether solution was concentrated to provide the crude title compound. Distillation of the product provided 82.6 g of pure title compound, b.p. 58°-61° C./5 mm.

Method b. Indirect Sequence.

1. 2-Acetoxy-5,5-dimethyl-1,3-cyclohexadiene.

To a solution of 465 g (3.75 moles) of 4,4-dimethyl-2-cyclohexenone in 1.5 liters of isopropenyl acetate were added 6 g of p-toluenesulfonic acid. Acetone slowly was distilled from the mixture overnight (about 16 hours) through a 14 inch Vigreaux column. The temperature then was increased to remove by distillation the bulk of the remaining isopropenyl acetate. The resulting mixture then was distilled at reduced pressure to yield 484 g of crude title compound, b.p. 45°-65° C./4 mm. The product was purified by redistillation to obtain pure title compound, b.p. 80°-84° C./7 mm.

2. 6-Bromo-4,4-dimethyl-2-cyclohexenone.

To a solution of 484 g (2.92 moles) of 2-acetoxy-5,5-dimethyl-1,3-cyclohexadiene in 4 liters of carbon tetrachloride were added 421 g (2.92 moles) of N-bromosuccinimide (NBS) followed by 0.5 grams of azo-bis-isobutyronitrile (AIBN). The resulting mixture was stirred and refluxed for 2 hours. After cooling, the major portion of the carbon tetrachloride was removed in vacuo. The residue then was dissolved in ether, and the ether solution was washed twice with aqueous sodium bicarbonate solution. The ether solution then was dried over sodium sulfate, and the solvent was removed in vacuo. The resulting residue was distilled to give 396 g (68%) of the title compound, b.p. 90°-102° C./2 mm.

3. 4,4-dimethyl-2,5-cyclohexadienone.

A solution of 218 g (1.09 moles) of 6-bromo-4,4-dimethyl-2-cyclohexenone in 1000 ml of dry hexamethylphosphoric triamide (HMPT) was heated at 80° C. under nitrogen for 5 hours. After cooling, the mixture was added to 3 liters of NaCl solution. The product was extracted using four portions of ether. The ether extracts were washed twice with saturated NaCl solution. The ether was removed under vacuum, and the product was distilled, $b_{15}$ 83°-87° C. Yield: 86 g (65%).

Preparation C. 4-Ethyl-4-methyl-2-cyclohexenone.

To 200 ml. of benzene were added 35.0 ml. (30.8 grams) of methyl vinyl ketone (freshly distilled at 40° C./155 mm.) and 50.0 ml. (40.1 grams) of α-methylbutyraldehyde. The mixture was cooled in an ice bath, and 0.5 ml. of concentrated sulfuric acid was added. The mixture slowly was brought to reflux over a one hour period and then was refluxed for three hours in a system containing a Dean-Stark water trap. The mixture then was added to an ice cold saturated sodium bicarbonate solution, and the total was extracted with ether. The ether extract was separated and was washed with saturated aqueous sodium chloride and then was dried over sodium sulfate. The ether was removed using a rotary evaporator, and the residue was distilled at reduced pressure to obtain 38.5 grams (64.6%) of the title compound, boiling point 73°-78° C./7 mm.

ir ($CHCl_3$) 1668 cm$^{-1}$ (C=O); λmax (MeOH) 228 nm (ε 16,050); nmr ($CDCl_3$) δ 0.92 (t, J=7Hz, 3H, Et), 1.12 (s, 3H, $CH_3$), 1.51 (qt, J=7Hz, 2H, Et), 1.85 (mult, 2H, β-CH$_2$), 2.45 (t, J=7Hz, 2H, α-CH$_2$), 5.84 (d, J=10Hz, 1H, β-CH), 6.68 (d, J=10Hz, 1H, α-CH).

Analysis, Calculated for C$_9$H$_{14}$O: C, 78.21; H, 10.21; Found: C, 77.97; H, 9.95

Preparation D.
4-Ethyl-4-methyl-2,5-cyclohexadienone.

To 300 ml. of toluene were added 35.0 grams (0.25 moles) of the product from Preparation C and 62.4 grams (0.275 moles) of 2,3-dichloro-4,5-dicyanobenzoquinone (DDQ). The resulting mixture was refluxed under nitrogen for four hours. The mixture then was cooled, and the 2,3-dichloro-4,5-dicyanohydroquinone (DDH) which was formed was collected by filtration. The filtrate was treated in a rotary evaporator to remove the major portion of the toluene. The resulting residue then was dissolved in ether, and the ether solution was washed several times with 1N sodium hydroxide and then with water. The ether layer then was dried over anhydrous sodium sulfate, and the ether was removed using a rotary evaporator. The residue was distilled to obtain 23.5 grams (69%) of the title compound, b.p. 86°-93° C./7 mm.

ir (CHCl$_3$) 1667 (C=O), 1627 cm$^{-1}$ (C=C); λmax (MeOH) 237 nm (ε 13,900); nmr (CDCl$_3$) δ 0.61 (t, J=7Hz, 3H, Et), 1.25 (s, 3H, CH$_3$), 1.69 (qt, J=7Hz, 2H, Et), 6.28 (d, J=10Hz, 2H, β-CH), 6.80 (d, J=10Hz, 2H, β-CH).

Analysis, Calculated for C$_9$H$_{12}$O: C, 79.37; H, 8.88; Found C, 79.65; H, 8.66

Preparation E. 4-Cyclohexanespiro-2-cyclohexenone.

A solution of 54.3 ml. (0.5 mole) of cyclohexanecarboxaldehyde and 40.5 ml. (0.5 mole) of freshly distilled methyl vinyl ketone in 200 ml. of benzene was stirred at room temperature, and 0.5 ml. of concentrated sulfuric acid was carefully added. The resulting mixture was gradully warmed to reflux over a period of about one hour. The mixture was refluxed for three hours, water continuously being removed by use of a Dean-Stark water trap. The mixture then was permitted to cool and was washed with dilute sodium bicarbonate solution. The washings were extracted with ether, and the combined organic mixture was dried over sodium sulfate. The solvents were removed under reduced pressure, and the residual oil was distilled to afford 46.8 grams (56%) of the title compound, b.p. 122°-126° C./5 mm.

ir (CHCl$_3$) 1670 cm$^{-1}$ (C=O); nmr (CDCl$_3$) δ 1.52 [s, 10H, (CH$_2$)$_5$], 1.90 (t, J=7Hz, 2H, β:CH$_2$), 2.44 (t, J=7Hz, 2H, α-CH$_2$), 5.89 (d, J=10Hz, 1H, β-CH), 6.87 (d, J=10Hz, 1H, α-CH).

Analysis, Calculated for C$_{11}$H$_{16}$O: C, 80.44; H, 9.82. Found: C, 80.18; H, 9.99.

Preparation F.
4-Cyclohexanespiro-2,5-cyclohexadienone.

A mixture of 16.4 grams (0.1 mole) of the product from Preparation E and 25 grams (0.12 mole) of DDQ in 150 ml. of toluene was refluxed under nitrogen for 6 hours. The resulting mixture then was cooled and filtered. The major portion of the toluene then was removed from the filtrate at reduced pressure. The resulting residue was dissolved in ether. The solution was washed twice with 1N sodium hydroxide, once with saturated aqueous sodium chloride, and then was dried over sodium sulfate. The solvent was removed, and the residue was recrystallized from hexane to afford 9.9 grams (61%) of the title compound as a light yellow solid, m.p. 86°-88° C.

ir (CHCl$_3$) 1663 (C=O), 1622 cm$^{-1}$ (C=C); λmax (MeOH) 242 nm (ε 14,800); nmr (CDCl$_3$) δ 1.60 [s, 10H, (CH$_2$)$_5$], 6.27 (d, J=10Hz, 2H, β-CH), 7.98 (d, J=10Hz, 2H, α-CH).

Analysis, Calculated for C$_{11}$H$_{14}$O: C, 81.44; H, 8.70. Found: C, 80.50; H, 8.32.

The following examples are provided to illustrate preparation of certain of the compounds of this invention. They are not intended to be limiting upon the scope of this invention.

Example 1.
(5aα,6aα)-6,6a-Dihydro-6,6-dimethyl-5aH,13H-(1)benzopyrano(3,2-b)xanthen-13-one.

A solution of 30 g (0.25 mole) of salicylaldehyde in 150 ml of benzene was cooled under nitrogen as it was treated first with 26.25 g (0.37 mole) of pyrrolidine, and then with 15 ml (0.25 mole) of acetic acid. After 15 min. at room temperature, 15 g (0.125 mole) of 4,4-dimethyl-2,5-cyclohexadienone was added, and the mixture was heated at 60° C. overnight. After cooling, the mixture was poured into a large volume of ice water. The organic layer was separated and washed twice with 1% aqueous acetic acid and then three times with 1M NaOH solution. After a final wash with saturated NaCl solution, the organic solution was dried over sodium sulfate. The solvent was removed, and the product was recrystallized from benzene-Skelly B. Yield after two recrystallizations: 18.6 g (46%), m.p. 211°-213° C.

ir (CHCl$_3$) 1670 (C=O), 1623 cm$^{-1}$ (C=C); λmax (EtOH) 253 (ε 12,400), 119 (ε 13,300), 378 nm (ε 10,300); nmr (CDCl$_3$) δ 1.19 (s, 3H, 6α-CH$_3$), 1.49 (s, 3H, 6β-CH$_3$), 4.89 (d, J=2.3 Hz, 2H, 5a-H and 6a-H), 7.07 (m, 8H, Ar-H), 7.60 (d, J=2.3 Hz, 2H, 12-H and 14-H).

Analysis, Calculated for C$_{22}$H$_{18}$O$_3$: C, 79.98; H, 5.49. Found: C, 79.76; H, 5.69.

Example 2.
(5aα,6aα,12aα,13aα)-6,6a,12,12a,13a,14-Hexahydro-6,6-dimethyl-5aH,13H-(1)benzopyrano(3,2-b)xanthen-13-one.

A solution of 4.0 g (12.1 mmoles) of the product of Example 1 in 500 ml. of ethyl acetate was hydrogenated over 4 g of Raney nickel [prepared according to the procedure of A. W. Burgstahler reported in L. Fieser and M. Fieser, *Reagents for Organic Synthesis*, 1, p. 729, John Wiley & Sons, Inc. (1967)] at 40°-60° C. and at 60 p.s.i. for 5-12 hours. After filtering, the solvent was removed. The product was recrystallized from ethanol-water. Yield: 2.45 g (61%), m.p. 205°-207° C.

ir (CHCl$_3$) 1732 cm$^{-1}$ (C=O); λmax (EtOH) 275 (ε 4,300), 283 sh nm (ε 3,500); nmr (CDCl$_3$) δ 1.37 (s, 3H, 6α-CH$_3$), 1.56 (s, 3H, 6δ-CH$_3$), 2.67 (broadened qt, J's=7 and 17 Hz, 2H, 12β-H and 14β-H), 3.24 (broadened qt, 2H, 12a-H and 13a-H), 3.34 (broadened d, J=17 Hz, 2H, 12α-H and 14α-H), 4.18 (d, J=2.8 Hz, 2H, 5a-H and 6a-H), 6.87 (m, 8H, Ar-H).

Analysis, Calculated for C$_{22}$H$_{22}$O$_3$: C, 79.02; H, 6.63. Found: C, 78.76; H, 6.63.

Example 3.
(5aα,6aα)-6,6a-Dihydro-2,10-dimethoxy-6,6-dimethyl-5aH,13H-(1)benzopyrano(3,2)xanthen-13-one.

A solution of 12.5 g (82 mmoles) of 5-methoxysalicylaldehyde in 100 ml of benzene was cooled as 8.73 g (123 mmoles) of pyrrolidine followed by 4.92 g (82 mmoles) of acetic acid were added. After stirring the mixture at room temperature for several minutes, 5.0 g (41 mmoles) of 4,4-dimethyl-2,5-cyclohexadienone were added. The mixture then was heated under nitrogen at 60° C. overnight after which it was added to ice water, and the resulting organic layer was separated. The organic layer then was washed successively with dilute acetic acid, several times with dilute sodium hydroxide, and then with sodium chloride solution. The organic layer was dried over sodium sulfate, and the solvent was removed. The residue was recrystallized twice from a mixture of benzene and Skelly B to afford 3.75 g (23%) of the title compound, m.p. 219°–220° C.

ir (CHCl$_3$) 1663 (C=O), 1620 cm$^{-1}$ (C=C); λmax (EtOH) 221 (ε 36,200), 336 (ε 20,400), 472 (ε 11,600), 453 sh nm (ε 11,400); nmr (CDCl$_3$) δ 1.18 (s, 3H, 6α-CH$_3$), 1.48 (s, 3H, 6β-CH$_3$), 3.76 (s, 6H, OCH$_3$), 4.83 (d, J=2.1 Hz, 2H, 5a-H and 6a-H), 6.78 (m, 6H, Ar-H), 7.55 (d, J=2.1 Hz, 12-H and 14-H).

Analysis, Calculated for C$_{24}$H$_{22}$O$_5$: C, 73.83; H, 5.68. Found: C, 73.95; H, 5.88.

Example 4.
(5aα,6aα)-6,6a-Dihydro-3,9-dimethoxy-6,6-dimethyl-5aH,13H-(1)benzopyrano(3,2-b)xanthen-13-one.

A solution of 14.35 g (94.4 mmoles) of 4-methoxysalicylaldehyde in 100 ml of benzene was prepared. The solution was cooled, and 10 g (141 mmoles) of pyrrolidine and 5.66 g (94.4 mmoles) of acetic acid were added. After several minutes, 5 g (41 mmoles) of 4,4-dimethyl-2,5-cyclohexadienone were added. The solution then was warmed under nitrogen at 55° C. overnight. The resulting reaction mixture then was added to ice water, and the organic layer was separated. The organic layer then was washed successively with dilute acetic acid, several times with dilute sodium hydroxide, and then with sodium chloride solution. The organic layer was dried over sodium sulfate, and the solvent was removed. The residue was recrystallized from a mixture of benzene and hexane and chromatographed on Florosil, eluting with benzene, to obtain 1.5 g of the title compound, m.p. 220°–221° C.

ir (CHCl$_3$) 1660 (C=O), 1608 cm$^{-1}$ (C=C); λmax (EtOH) 213 (ε 38,400), 276 (ε 16,900), 460 (ε 23,900), 466 sh nm (ε 22,800); nmr (CDCl$_3$) δ 1.18 (s, 3H, 6α-CH$_3$), 1.49 (s, 3H, 6β-CH$_3$), 3.82 (s, 6H, OCH$_3$), 4.88 (d, J=2.1 Hz, 2H, 5a-H and 6a-H), 6.44 (m, 4H, Ar-H), 7.10 (m, 2H, Ar-H), 7.55 (d, J=2.1 Hz, 2H, 12-H and 14-H).

Analysis, Calculated for C$_{24}$H$_{22}$O$_5$: C, 73.83; H, 5.68. Found: C, 73.79; H, 5.78.

Example 5.
(5aα,6aα)-6,6a-Dihydro-4,8-dimethoxy-6,6-dimethyl-5aH,13H-(1)benzopyrano(3,2-b)xanthen-13-one.

A solution of 100 g (0.66 mole) of 3-methoxysalicylaldehyde in 800 ml. of benzene was cooled under nitrogen as it was treated first with 80 g (1.15 mmoles) of pyrrolidine, and then with 60 g (1.0 mole) of acetic acid. After 15 minutes at room temperature, 40 g (0.33 mole) of 4,4-dimethyl-2,5-cyclohexadienone were added, and the mixture was heated at 55°–60° C. overnight. After cooling, the mixture was poured into a large volume of ice water. The organic layer was washed twice with 1% aqueous acetic acid and then three times with 1M sodium hydroxide solution. After a final wash with saturated sodium chloride solution, the organic solution was dried over sodium sulfate. The solvent was removed, and the product was recrystallized from a mixture of benzene and Skelly B to afford 43 g (33%) of the title compound, m.p. 239°–241° C.

ir (CHCl$_3$) 1664 (C=O), 1619 cm$^{-1}$ (C=C); λmax (EtOH) 225 (ε 35,400), 358 (ε 18,300), 436 (ε 8,300), 454 sh nm (ε 6,500); nmr (CDCl$_3$) δ 1.26 (s, 3H, 6αCH$_3$), 1.61 (s, 3H, 6β-CH$_3$), 3.88 (s, 6H, OCH$_3$), 4.94 (d, J=2.3 Hz, 2H, 5a-H and 6a-H), 6.86 (s, 6H, Ar-H), 7.59 (d, J=2.3 Hz, 2H, 12-H and 14-H).

Analysis, Calculated for C$_{24}$H$_{22}$O$_5$: C, 73.83; H, 5.68. Found: C, 73.79; H, 5.62.

Example 6.
(5aα,6aα,12aα,13aα)-6,6a,12,12a,13a,14-Hexahydro-2,10-dimethoxy-6,6-dimethyl-5aH,13H-(1)benzopyrano(3,2-b)xanthen-13-one.

A solution of 1.0 g (2.56 mmoles) of the product of Example 3 in ethyl acetate was hydrogenated over Raney nickel for 24 hours. The mixture was filtered, and the filtrate was evaporated to accomplish removal of the solvent. The resulting residue was recrystallized twice from a mixture of methanol and water. The dried product, m.p. 174°–178° C., weighed 0.59 g (58%). Analysis of the product by NMR indicated that it was a mixture of epimers of the title compound as well as some product which has been over-reduced to the corresponding alcohol.

A portion of the above product (0.35 g) was stirred overnight in 10 ml. of methylene chloride containing 0.3 g of pyridinium chlorochromate under nitrogen. To the mixture then were added 10 ml. of benzene, and the mixture was stirred for an additional 1 hour. The mixture then was filtered, and the solid which was collected was thoroughly washed with benzene which was added to the filtrate. The solvent in the filtrate was removed, and the resulting residue was dissolved in ethyl acetate. The ethyl acetate solution then was passed through a short florosil column. The effluent solvent was removed, and the resulting residue was recrystallized from a mixture of benzene and Skelly B to obtain 0.18 g (51%) of dried, slightly impure title compound.

A six foot long, ⅜ inch diameter high pressure liquid chromatography (HPLC) column was packed dry with about 150 grams of 10–20 μ silica gel. The column was equilibrated with a 20:80 mixture of tetrahydrofuran (THF) and isooctane. Portions (about 30 mg.) of the above, slightly impure product in methylene chloride were added to the column. A total of about 173 mg. of the product was passed through the column in 7 runs. A total of 137 mg., representing an overall yield of 30%, of dried, purified title compound was collected after crystallization of the product from Skelly B, m.p. 207°–207.5° C.

ir (CHCL$_3$) 1727 cm$^{-1}$ (C=O); λmax (MeOH) 229 nm (ε 13,800); nmr (CDCl$_3$) δ 1.37 (s, 3H, 6α-CH$_3$), 1.52 (s, 3H, 6β-CH$_3$), 2.68 (broadened qt, J's=7 and 17 Hz, 2H, 12β-H and 14β-H), 3.23 (broadened qt, 2H, 12a-H and 13a-H), 3.30 (broadened d, J=17 Hz, 2H, 12α-H and 14α-H), 3.67 (s, 6H, OCH$_3$), 4.12 (d, J=2.7 Hz, 2H, 5a-H and 6a-H), 6.57 (m, 6H, Ar-H).

Analysis, Calculated for C$_{24}$H$_{26}$O$_5$: C, 73.08; H, 6.64. Found: C, 72.84; H, 6.70.

Example 7.
(5aα,6aα12aα,12aβ,13aβ)-6,6a,12,12a,13a,14-Hexahydro-3,9-dimethoxy-6,6-dimethyl-5aH,13H-(1)benzopyrano(3,2)xanthen-13-one and (5aα,6aα,1-2aα,13aα)-6,6a,12,12a,13a,14-Hexahydro-3,9-dimethoxy-6,6-dimethyl-5aH,13H-(1)benzopyrano(3,2-b)xanthen-13-one.

Employing the hydrogenation procedure of Example 3, 0.5 g (12.8 mmoles) of (5aα,6aα)-6,6a-dihydro-3,9-dimethoxy-6,6-dimethyl-5aH,13H-(1)benzopyrano(3,2-b)xanthen-13-one was reduced over Raney nickey in ethyl acetate. The mixture was filtered, and the solvent was removed in vacuo. The resulting yellowish residue was recrystallized twice from a mixture of ethanol of ethanol and water. The yield of dried product, m.p. 217° C., was 0.31 g (61%). NMR analysis of the dried product indicated that it was a mixture of the above title compounds in a ratio of about 1:4, respectively.

Analysis, Calculated for $C_{24}H_{26}O_5$: C, 73.08; H, 6.64. Found: C, 73.23; H, 6.40.

A six foot long, ⅝ inch diameter HPLC column was packed dry with about 150 grams of 10–20 μ silica gel. The column then was equilibrated with a 30:70 mixture of THF and isooctane. Using this system at a flow rate of 5–6 ml./min. at about 300 psig, the above mixture was separated. The mixture was placed on the column in portions of about 10–15 mg. dissolved in about 0.75 ml. of THF. In all, six runs were made totalling about 70 mg. The two purified components were crystallized from Skelly B, collected, and dried. There were obtained 15 mg. (13% yield overall) of the α,α,β,β compound, m.p. 219° C., and 44 mg. (38% yield overall of the α,α,α,α compound, m.p. 230°–231° C.

α,α,β,β compound — ir ($CHCl_3$) 1727 cm$^{-1}$ (C=O); λmax (MeOH) 283 (ε 7,800), 289 nm (ε 7,400); nmr ($CDCl_3$) δ 1.32 (s, 3H, 6α-$CH_3$), 1.47 (s, 3H, 6β-$CH_3$), 2.90 (m, 6H, H's at 12, 12a, 13a and 14), 3.54 (m, 2H, 5a-H and 6a-H), 3.77 (s, 6H, $OCH_3$), 6.45 (d, J=2.5 Hz, 2H, 4-H and 8-H), 6.48 (qt, J's=2.5 and 9 Hz, 2H, 2-H and 10-H), 7.02 (d, J=9 Hz, 2H, 1-H and 11-H).

α,α,α,α compound — ir ($CHCl_3$) 1727 cm$^{-1}$ (C=O); λmax (MeOH) 284 (ε 6,500), 291 nm (ε 6,000); nmr ($CDCl_3$) δ 1.39 (s, 3H, 6α-$CH_3$), 1.55 (s, 3H, 6β-$CH_3$), 2.63 (broadened qt, J's=7 and 16 Hz, 2H, 12β-H and 14β-H), 3.23 (broadened qt, 2H, 12a-H and 13a-H), 3.26 (broadened d, J=16 Hz, 2H, 12α-H and 14α-H), 3.69 (s, 6H, $OCH_3$), 4.18 (d, J=2.8, 2H, 5a-H and 6a-H), 6.27 (d, J=2.5 Hz, 2H, 4H and 8-H), 6.36 (qt, J's=2.5 and 8 Hz, 2H, 2-H and 10-H), 6.91 (d, J=8 Hz, 2H, 1-H and 11-H).

Example 8.
(5aα,6aα)-6,6a-Dihydro-4,8-dihydroxy-6,6-dimethyl-5aH,13H-(1)benzopyrano(3,2-b)xanthen-13-one.

A solution of 5.0 g (12.8 mmoles) of (5aα,6aα)-6,6a-dihydro-4,8-dimethoxy-6,6-dimethyl-5aH,13H-(1)benzopyrano(3,2-b)xanthen-13-one from Example 5 in 100 ml of methylene chloride was stirred under nitrogen with ice-methanol cooling. A solution of 5 ml of boron tribromide was added dropwise over a 10 minute period. The bath then was removed, and the resulting intense violet mixture was stirred overnight. The mixture was added to ice water. Ethyl acetate was added, and the two phases were vigorously stirred for about one hour. The organic layer was separated. The aqueous phase was extracted twice with fresh ethyl acetate. The extracts were filtered and dried over sodium sulfate. The solvents were removed, and the crude product was recrystallized from acetone and water to obtain the title compound. Yield: 3.59 g (77%), m.p. >230° C. dec.

ir (KBr) 1660 (C=O), 1613 cm$^{-1}$ (C=C); λmax (MeOH) 223 (ε 41,600), 363 (ε 24,050), 433 sh (ε 10,100), 455 sh nm (ε 8,000); nmr (DMSO-$d_6$)δ 1.14 (s, 3H, 6α-$CH_3$), 1.61 (s, 3H, 6β-$CH_3$), 4.98 (d, J=2.0 Hz, 2H, 5a-H and 6a-H), 6.88 (s, 6H, Ar-H), 7.57 (d, J=2.0 Hz, 2H, 12-H and 14-H), 9.27 (s, 2H, OH).

Analysis, Calculated for $C_{22}H_{18}O_5$: C, 72.92; H, 5.01. Found: C, 72.66; H, 5.23.

Example 9.
(5aα,6aα,12aα,13aα)-6,6a,12,12a,13a,14-Hexahydro-4,8-dihydroxy-6,6-dimethyl-5aH,13H-(1)benzopyrano(3,2-b)xanthen-13-one.

A solution of 1.0 gram of the product of Example 8 was dissolved in ethyl acetate and was hydrogenated over 1 gram of freshly prepared Raney nickel. Hydrogenation was carried out for one hour at room temperature and at 60 psig. The mixture was filtered, and the filtrate was evaporated to accomplish removal of the solvent. The resulting residue was crystallized from a mixture of benzene and ethyl acetate. The product was collected and recrystallized again from benzene-ethyl acetate to obtain 0.15 gram (about 15% yield) of the title compound, m.p. 194°–198° C.

ir (mull) 3520 (OH), 1720 cm$^{-1}$ (C=O); λmax (MeOH) 277 (ε 3,400), 283 nm (ε 3,300); nmr (DMSO-$d_6$) δ 1.48 (s, 3H, 6α-$CH_3$), 1.66 (s, 3H, 6β-$CH_3$), 2.86 (broadened qt, J's=7 and 13 Hz, 12β-H and 14β-H), 3.36 (s, OH), 3.52 (broad m, 4H, 12α-H, 13a-H, and 14α-H, 4.26 (d, 2H, 5a-H and 6a-H), 6.59 (m, 6H, Ar-H).

Analysis, Calculated for $C_{22}H_{22}O_5$: C, 72.12; H, 6.05. Found: C, 71.91; H, 5.86.

Example 10.
(5aα,6aα)-6,6a-Dihydro-4,8-diethoxy-6,6-dimethyl-5aH,13H-(1)benzopyrano(3,2-b)xanthen-13-one.

A solution of 1.0 g (2.76 mmoles) of (5aα,6aα)-6,6a-dihydro-4,8-dihydroxy-6,6-dimethyl-5aH,13H-(1)benzopyrano(3,2-b)xanthen-13-one in 25 ml. of dye hexamethylphosphoric triamide (HMPT) was treated with 1 g (7.25 mmoles) of potassium carbonate and 2 ml. (2.9 g; 27 mmoles) of ethyl bromide. The mixture was heated under nitrogen at 70° C. overnight. After cooling, the mixture was poured into 200 ml. of cold water. The resulting product was collected and recrystallized twice from ethanol-water. There was obtained 0.54 g (47% yield) of the title compound, m.p. 211°–213° C.

ir ($CHCl_3$( 1680 (C=O), 1635 cm$^{-1}$ (C=C); λmax (MeOH) 224 (ε 41,200), 356 (ε 19,800), 434 (ε 9,100), 456 sh nm (ε 7,200); nmr ($CDCl_3$) δ 1.26 (s, 3H, 6α-$CH_3$), 1.42 (t, J=7 Hz, 6H, OEt), 1.59 (s, 3H, 6β-$CH_3$), 4.06 (qt, J=7 Hz, 4H, OEt), 4.90 (d, J=2.3 Hz, 2H, 5a-H and 6a-H), 6.87 (m, 6H, Ar-H), 7.58 (d, J=2.3 Hz, 2H, 12-H and 14-H).

Analysis, Calculated for $C_{26}H_{26}O_5$: C, 74.62; H, 6.26. Found: C, 74.92; H, 6.51.

Example 11.
(5aα,6aα,12aα,13aα)-6,6a,12,12a,13a,14-Hexahydro-4,8-diethoxy-6,6-dimethyl-5aH,13H-(1)benzopyrano(3,2-b)xanthen-13-one.

A solution of 0.45 g of the product of Example 10 in ethyl acetate was hydrogenated over Raney nickel for 24 hours. The resulting mixture then was filtered, and the filtrate was evaporated to a pale yellow, solid residue. The resulting crude product was dissolved in 10 ml of methylene chloride. To the resulting solution then was added 0.3 grams of pyridinium chlorochromate, and the resulting mixture was stirred under nitrogen overnight. The resulting mixture was then diluted with 10 ml of benzene, stirred for one hour, and decanted. The solvents were removed, and the residue, dissolved in ethyl acetate, was filtered through a short Florosil column. Thin-layer chromatography (TLC) showed primarily one spot material with a very faint trace of two other components. The product was recrystallized from a mixture of benzene and Skelly B. The resulting product was collected and dried to afford 0.23 g (51%) of the title compound, m.p. 219°14 221° C.

ir (mull) 1735 cm$^{-1}$ (C=O); λmax (MeOH) 277 (ε 3,300), 282 nm (ε 3,330); nmr (CDCl$_3$) δ 1.28 (t,m J=7 Hz, 6H, OEt), 1.45 (s, 3H, 6α-CH$_3$), 1.67 (s, 3H, 6β-CH$_3$), 2.73 (qt, J's=8 and 17 Hz, 2H, 12β-H and 14β-H), 3.32 (qt, J's=2.8 and 8 Hz, 2H, 12a-H and 13a-H), 3.40 (d, J=17 Hz, 2H, 12α-H and 14α-H), 4.03 (m, 4H, OEt), 4.16 (d, J=2.8 Hz, 2H, 5a-H and 6a-H), 6.68 (m, 6H, Ar-H).

Analysis, Calculated for C$_{26}$H$_{30}$O$_5$: C, 73.91; H, 7.16. Found: C, 73.98; H, 7.10.

Example 12.
(5aα,6aα,12aα,13aα)-6,6a,12,12a,13a,14-Hexadhydro-4,8-dimethoxy-6,6-dimethyl-5aH,13H-(1)benzopyrano(3,2-b)xanthen-13-one.

A mixture of 200 g of (5aα,6aα)-6,6a-dihydro-4,8-dimethoxy-6,6-dimethyl-5aH,13H-(1)benzopyrano(3,2-b)xanthen-13-one in 3.7 liters of tetrahydrofuran (THF) was hydrogenated at an initial hydrogen pressure of 50-60 psi and at 50°-60° C. for 24 hours in the presence of 100 g of PtO$_2$. The reaction mixture then was cooled, and the catalyst was removed by filtration and washed well with methylene chloride. The methylene chloride wash was added to the filtrate, and the filtrate was concentrated in vacuo. The resulting residue was triturated with hexane to provide the hexahydro compound in which the carbonyl group in the 13-position had been reduced to a hydroxyl. The product was recovered as a crude colorless solid. Upon recrystallization from toluene-hexane, pure compound was obtained, m.p. 180°-181° C.

ir (CHCl$_3$) 3550 cm$^{-1}$ (OH); nmr (CDCl$_3$) δ 1.12 (s, 3H, 6α-CH$_3$), 1.66 (s, 3H, 6β-CH$_3$), 2.35 (broadened qt, J's=2 and 8Hz, 2H, 12a-H and 13a-H), 2.89 (d, J=17 Hz, 2H, 12α-H and 14α-H), 3.19 (broadened qt, J's=8 and 17Hz, 2H, 12β-H and 14β-H), 3.80 (broad s, 9H, OCH$_3$, 5a-H, 6a-H, and 13-H), 6.70 (mult, 6H, Ar-H).

Analysis, Calculated for C$_{24}$H$_{28}$O$_5$: C, 72.89; H, 6.88. Found: C, 73.01; H, 6.71.

To a 12 liter flask containing 3 liters of methylene chloride were added 250 g (0.16 mole) of pyridinium chlorochromate. The resulting suspension was stirred vigorously, and 250 g (0.63 moles) of the above product in 4 liters of methylene chloride were added rapidly at room temperature and under a nitrogen atmosphere. The mixture was stirred for 24 hours. Toluene (3 liters) then was added followed by 300 grams of decolorizing carbon. The resulting mixture then was filtered through a pad of Hyflo Cell. The filtrate was concentrated under reduced pressure, and the concentrate was passed through a column (30 cm. × 55 cm.) containing one kg. of silica gel packed with methylene chloride and eluted with methylene chloride. The eluant was concentrated under reduced pressure to yield crude title compound. The crude product was recrystallized from a mixture of methylene chloride and hexane to afford colorless needles (62% yield), m.p. 208°-209° C.

ir (mull) 1718 cm$^{-1}$ (C=O); λmax (EtOH) 275 (ε 3,660), 280 nm (ε 3,630); nmr (CDCl$_3$) δ 1.34 (s, 3H, 6α-CH$_3$), 1.65 (s, 3H, 6β-CH$_3$), 2.68 (broadened qt, J's=7 and 17 Hz, 2H, 12β-H and 14β-H), 3.26 (broadened qt, 2H, 12a-H and 13a-H), 3.37 (broadened d, J=17 Hz, 2H, 12α-H and 14α-H), 3.77 (s, 6H, OCH$_3$), 4.15 (d, J=2.8 Hz, 2H, 5a-H and 6a-H), 6.68 (s, 6H, Ar-H).

Analysis, calculated for C$_{24}$H$_{26}$O$_5$: C, 73.08; H, 6.64. Found: C, 72.83; H, 6.81.

Example 13.
(5aα,6aα,12aα,13aα)-6,6a,12,12a,13a,14-Hexahydro-4,8-dimethoxy-6,6-dimethyl-5aH,13H-(1)benzopyrano(3,2-b)xanthen-13-one.

A solution of 10 g (25.6 mmoles) of the product of Example 5 in 1 liter of ethyl acetate was hydrogenated over 10 g of Raney nickel [prepared according to the procedure of A. W. Burgstahler reported in L. Fieser and M. Fieser, *Reagents for Organic Synthesis*, 1, p. 729, John Wiley & Sons, Inc. (1967)] at 60° C. and at 60 p.s.i. for two hours. After filtering, the solvent was removed. The residue was dissolved in 200 ml of methylene chloride, and the solution was stirred overnight under nitrogen with 6.0 g of pyridinium chlorochromate. The mixture was diluted with 200 ml. of benzene. After stirring for 30 min., the mixture was suction filtered through Celite. The solvents were removed. The residue was passed through a short column of florosil and was eluted with benzene. Crystallization of the product from benzene-Skelly B give 7.1 g of a mixture determined by high pressure liquid chromatography (HPLC) to contain 70% of (5aα,6aα,12aα,13aα)-6,6a,12,12a,13a,14-hdexahydro-4,8-dimethoxy-6,6-dimethyl-5aH,13H-(1)benzopyrano(3,2-b)xanthen-13-one (1), 19% of (5aα,6aα,12aβ,13aβ)-6,6a,12,12a,13a,14-hexahydro-4,8-dimethoxy-6,6-dimethyl-5aH,13H-(1)benzopyrano(3,2-b)xanthen-13-one (2) and 11% of (5aα,6aα,12aα,13aβ)-6,6a,12,12a,13a,14-hexahydro-4,8-dimethoxy-6,6-dimethyl-5aH,13H-(1)benzopyrano(3,2-b)xanthen-13-one (3). Further recrystallizations produced a mixture containing 90% of (1) and 10% of (2). m.p. of mixture: 206°-210° C.

Example 14.
(5aα,6aα,12aβ1,13aβ)-6,6a,12,12a,13a,14-Hexahydro-4,8-dimethoxy-6,6-dimethyl-5aH,13H-(1)benzopyrano(3,2-b)xanthen-13-one.

The mother liquor obtained from the product purification in Example 13 and enriched in compounds (2) and (3) of Example 13 was purified by high pressure liquid chromatography (HPLC). A six foot long, 5/8 inch diameter HPLC column was packed dry with about 150 grams of 10-20 μ silica gel. The product mixture (100 mg.) was chromatographed in 6 separate portions using, as eluant, a 30:70 mixture of tetrahydrofuran and isooctane. By this method, the residual amounts of the title compound of Example 13 and other trace materials were removed. The fraction containing compounds (2) and (3) was rechromatographed, using as eluant, a 10:90 mixture of tetrahydrofuran and isooctane. The fraction containing the title compound was collected and evaporated. The residue was washed with Skelly B and dried overnight in vacuo to obtain 30 mg. of the title compound, m.p. 272°-273° C.

ir (KBr) 1720 cm$^{-1}$ (C=O); λmax (MeOH) 275 (ε 3,500), 280 sh nm (ε 3,300); nmr (CDCl$_3$) δ 1.40 (s, 3H, 6α-CH$_3$), 1.57 (s, 3H, 6β-CH$_3$), 2.97 (m, 6H, H's at 12, 12a, 13a, and 14), 3.54 (m, 2H, 5a-H and 6a-H), 3.85 (s, 6H, OCH$_3$), 6.76 (m, 6H, Ar-H).

Analysis, Calculated for C$_{24}$H$_{26}$O$_5$: C, 73.08; H, 6.64. Found: C, 73.34; H, 6.33.

Example 15.
(5aα,6aα)-6,6a-Dihydro-6β-methyl-6α-ethyl-5aH,13H-(1)benzopyrano(3,2-b)xanthen-13-one.

To 220 ml. of benzene were added with ice bath cooling 18.2 grams (149 mmoles) of salicyladehyde, 13.3 grams of pyrrolidine, and 8.9 grams of acetic acid. To the resulting solution then were added 10.0 grams (73.5 mmoles) of 4-ethyl-4-methyl-2,5-cyclohexadienone. The resulting mixture was allowed to stir at 55° C. under nitrogen for a total period of five days. The mixture then was cooled and was poured into a large volume of ice water. The resulting organic layer was separated, washed twice with 1% aqeuous acetic acid, three times with 1N sodium hydroxide, and once with saturated aqueous sodium chloride. The organic layer then was dried over sodium sulfate, and the benzene solvent was removed using a rotary evaporator. The residue was recrystallized from a mixture of benzene and Skelly B to obtain 4.6 grams (18.2%) of the title compound, m.p. 189°–190° C.

ir (mull) 1665 (C=O), 1622 cm$^{-1}$ (C=C); λmax (MeOH) 217 (ε 35,800), 257 (ε 11,700), 324 (ε 13,800), 430 nm (ε 11,800); nmr (CDCl$_3$) δ 1.03 (t, J=7Hz, 3H, Et), 1.20 (s, 3H, CH$_3$), 2.01 (qt, J=7Hz, 2H, Et), 5.07 (d, J=2Hz, 2H, 5a-H and 6a-H), 7.08 (m, 8H, Ar-H), 7.60 (d, J=2Hz, 2H, 12-H and 14-H).

Analysis, Calculated for C$_{23}$H$_{18}$O$_3$: C, 80.21; H, 5.85. Found: C, 80.48; H, 6.13.

Example 16.
(5aα,6aα,12aα,13aα)-6,6a,12,12a,13a,14-Hexahydro-6β-methyl-6α-ethyl-5aH,13H-(1)benzopyrano(3,2-b)xanthen-13-one.

A solution of 1.0 gram (0.29 mmole) of the product from Example 15 in 49 ml. of tetrahydrofuran was hydrogenated over 0.5 grams of platinum oxide at 50 p.s.i. and at room temperature for a total of 32 hours. The mixture was filtered, and the filtrate was evaporated in vacuo. The residue was chromatographed over silica gel using benzene as eluant. Crystallization from ether afforded 0.28 grams (27%) of the hexahydro compound having the carbonyl group in the 13-position reduced to a hydroxyl. The product was a colorless solid, m.p. 161°–162° C.

Analysis, Calculated for C$_{23}$H$_{26}$O$_3$: C, 78.83; H, 7.40. Found: C, 78.61; H, 7.27.

The above product (0.27 gram; 0.76 mmole) was dissolved and cooled in 5 ml. of acetic acid. A mixture of 20 mg. (0.5 mmoles) of sodium dichromate dihydrate in 10 ml. of acetic acid was cooled in an ice bath and then was added to the mixture. The resulting mixture was allowed to stir at room temperature for 4.5 hours. The mixture then was poured into about 100 ml. of cold water. The resulting precipitate was collected by filtration, and any remaining product was extracted from the aqueous filtrate with methylene chloride. The product was collected and purified by chromatographic separation over silica gel using benzene as eluant to obtain, after recrystallization from a mixture of benzene and Skelly B, 55.7 mg. (21%) of the title compound, m.p. 138°–140° C.

ir (CHCl$_3$) 1730 cm$^{-1}$ (C=O); λmax (MeOH) 276 (ε 3500), 283 nm (ε 3140); nmr (CDCl$_3$) δ 1.07 (t, J=7hz, 3H, Et), 1.52 (s, 3H, CH$_3$), 1.84 (qt, J=7Hz, 2H, Et), 2.71 (broadened qt, J's=7 + 17Hz, 2H, 12β-H and 14β-H), 3.24 (broadened qt, J's=2.5 + 7Hz, 2H, 12a-H and 13a-H), 3.35 (broadened d, J=17Hz, 2H, 12α-H and 14α-H), 4.26 (d, J=2.5Hz, 2H, 5a-H and 6a-H), 6.88 (m, 8H, Ar-H).

Analysis, Calculated for C$_{23}$H$_{22}$O$_3$: C, 79.28; H, 6.94. Found: C, 79.22; H, 6.70.

Example 17.
(5aα,6aα)-6,6a-Dihydro-4,8-dimethoxy-6β-methyl-6α-ethyl-5aH,13H-(1)benzopyrano(3,2-b)xanthen-13-one.

To 180 ml. of benzene were added with cooling 18.10 grams (119 mmoles) of 3-methoxysalicylaldehyde, 10.64 grams of pyrrolidine, and 7.12 grams of acetic acid. To the resulting solution were added 8.00 grams (58.6 mmoles) of 4-ethyl-4-methyl-2,5-cyclohexadienone. The resulting mixture was stirred for two days under nitrogen at 53° C. The mixture then was cooled and was poured into a large volume of ice water. The organic layer was separated and was washed twice with 1% aqueous acetic acid, three times with 1N sodium hydroxide, and then with saturated aqueous sodium chloride. The organic layer was dried over sodium sulfate, and the benzene was removed using a rotary evaporator. The residue was chromatographed over silica gel to obtain the title compound. Recrystallization from a mixture of chloroform and methanol afforded 2.18 grams (9.2%) of the title compound, m.p. 203°–205° C.

ir (CHCl$_3$) 1668 (C=O), 1622 cm$^{-1}$ (C=C); λmax (MeOH) 225 (ε 40,800), 356 (ε 20,400), 430 sh nm (ε 9340); nmr (CDCl$_3$) δ 1.12 (t, J=7Hz, 3H, Et), 1.25 (s, 3H, CH$_3$), 2.11 (qt, J=7Hz, 2H, Et), 3.85 (s, 6H, OCH$_3$), 5.05 (d, J=2Hz, 2H, 5a-H and 6a-H), 6.86 (s, 6H, Ar-H), 7.58 (d, J=2Hz, 2H, 12-H and 14-H).

Analysis, Calculated for C$_{25}$H$_{24}$O$_5$: C, 74.24; H, 5.98. Found: C, 74.46; H, 5.97.

Example 18.
(5aα,6aα,12aα,13aα)-6,6a,12,12a,13a,14-Hexahydro-4,8-dimethoxy-6β-methyl-6α-ethyl-5aH,13H-(1)benzopyrano(3,2-b)xanthen-13-one.

A solution of 1.0 gram (0.25 mmole) of the product from Example 17 in 49 ml. of tetrahydrofuran was hydrogenated over 0.5 gram of platinum oxide at 50 p.s.i. and at room temperature for 16 hours. The catalyst was removed by filtration. The filtrate was evaporated in vacuo, and the residue was recrystallized from a mixture of benzene and Skelly B to obtain 0.41 grams (40%) of the hexahydro compound in which the carbonyl group in the 13-position had been reduced to a hydroxyl, m.p. 222°–223° C.

ir (CHCl$_3$) 3550 cm$^{-1}$ (OH); λmax (MeOH) 274 nm (ε 2760).

Analysis, Calculated for C$_{25}$H$_{30}$O$_5$: C, 73.15; H, 7.37. Found: C, 72.91; H, 7.53.

To 6 ml. of acetic acid were added 400 mg. (0.98 mmole) of the above alcohol. The mixture was cooled in an ice bath and then was treated with a previously chilled solution of 258 mg. of sodium dichromate dihydrate in 13 ml. of acetic acid. The mixture was maintained for 4 hours and then was poured into 150 ml. of cold water. The resulting precipitate was too fine to be collected; therefore, it was extracted with several portions of methylene chloride. The methylene chloride extract was dried over sodium sulfate, and the solvent was removed by evaporation. The residue was dissolved in a small portion of ethyl acetate and was placed on a small column of Florosil. The product was collected; however, it would not crystallize. The product was chromatographed over silica gel using benzene as eluant. The recovered material was collected and recrystallized from a mixture of benzene and Skelly B to obtain the title compound as colorless crystals, m.p. 191°–192° C.

ir (CHCl$_3$) 1733 cm$^{-1}$ (C=O); λmax (MeOH) 276 (ε 3070), 281 sh nm (ε 3030); nmr (CDCl$_3$) ε 1.11 (t, J=7Hz, 3H, Et), 1.64 (s, 3H, CH$_3$), 1.90 (qt, J=7Hz, 2H, Et), 2.75 (broadened qt, J's=8 + 17Hz, 2H, 12β-H and 14β-H), 3.31 (broadened qt, J's=8 + 2.5Hz, 2H, 12a-H and 13a-H), 3.39 (broadened d, J=17Hz, 2H, 12α-H and 14α-H), 3.78 (s, 6H, OCH$_3$), 4.29 (d, J=2.5Hz, 2H, 5a-H and 6a-H), 6.68 (m, 6H, Ar-H).

Analysis, Calculated for C$_{25}$H$_{28}$O$_5$: C, 73.51; H, 6.91. Found: C, 73.28; H, 7.00.

Example 19.
(5aα,6aα-Dihydrospiro[5aH,13H-(1)benzopyrano(3,2-b)xanthene-6,1'-cyclohexan]-13-one.

To 85 ml. of benzene were added 7.52 grams (61.6 mmoles) of salicylaldehyde, 5.5 grams of pyrrolidine, and 3.7 grams of acetic acid. The mixture was cooled, and 5.00 grams (30.8 mmoles) of 4-cyclohexanespiro-2,5-cyclohexadienone were added. The mixture then was allowed to stir for two days at 55° C. under nitrogen. The mixture then was cooled and was poured into a large volume of ice water. The resulting organic layer was separated and was washed twice with 1% aqueous acetic acid, three times with 1N sodium hydroxide, and then with saturated aqueous sodium chloride. The organic layer was dried over sodium sulfate, and the benzene was removed using a rotary evaporator. The residue was recrystallized from methanol; however, a considerable amount of product was retained in the mother liquor. The mother liquor therefore was concentrated, and the residue was chromatographed over silica gel using benzene as eluant. The combined product (recrystallized and chromatographed materials) then was recrystallized from a mixture of chloroform and methanol to afford 3.62 grams (32%) of the title compound, m.p. 162°–163° C.

ir (CHCl$_3$) 1671 (C=C), 1622 cm$^{-1}$ (C=C); λmax (MeOH) 218 (ε 35,800), 256 (ε 9900), 322 (ε 13,100), 388 nm (ε 12,900); nmr (CDCl$_3$) δ 1.8 (broad m, 10H, CH$_2$), 5.03 (d, J=2Hz, 2H, 5a-H and 6a-H), 7.1 (m, 8H, Ar-H), 7.53 (d, J=2Hz, 2H, 12-H and 14-H).

Analysis, Calculated for C$_{25}$H$_{22}$O$_3$: C, 81.06; H, 5.99. Found: C, 81.13; H, 6.12.

Example 20.
(5aα,6aα,12aα,13aα)-6,6a,12,12a,13a,14 Hexahydrospiro[5aH,13H-(1)benzopyrano(3,2-b)xanthene-6,1'-cyclohexan]-13-one.

A solution of 2.0 grams (0.55 mmoles) of the product from Example 19 in 97 ml. of tetrahydrofuran was hydrogenated over 1.0 gram of platinum oxide at 50 p.s.i. and at room temperature for 16 hours. The catalyst was removed from the mixture by filtration, and the filtrate was evaporated in vacuo. The residue was recrystalized from a mixture of benzene and Skelly B to obtain 1.10 grams (54%) of the hexahydro compound in which the carbonyl group in the 13-position had been reduced to a hydroxyl, m.p. 236°–238° C.

ir (CHCl$_3$) 3580 cm$^{-1}$(OH); λmax (MeOH) 277 nm (ε 4150).

Analysis, Calculted for C$_{25}$H$_{28}$O$_3$: C, 79.76; H, 7.50. Found: C, 79.49; H, 7.68.

To 20 ml. of acetic acid was added 1.00 gram (2.66 mmole) of the above alcohol. The mixture was chilled in an ice bath, and a chilled solution of 0.70 gram (1.75 mmole) of sodium dichromate dihydrate in 35 ml. of acetic acid was added. The mixture was maintained at room temperature for 4 hours and then was slowly poured into 500 ml. of cold water. The resulting precipitate was collected by filtration. The material then was dissolved in a small amount of ethyl acetate and was chromatographed over Florosil using ethyl acetate and eluant. The ethyl acetate fractions were evaporated, and the residue was recrystallized from a mixture of benzene and hexane to afford 385 mg. (38%) of the title compound, m.p. 226° C.

ir (null) 1720 cm$^{-1}$ (C=O); λmax (MeOH) 274 (ε 3450), 282 nm (ε3450).

Analysis, Calculated for C$_{25}$H$_{24}$O$_3$: C, 80.18; H, 7.00. Found: C, 80.43; H, 6.77.

Example 21.
(5aα,6aβ)-6,6a-Dihydro-6,6-dimethyl-5aH,13H-(1)-benzopyrano(3,2-b)xanthen-13-one.

A solution of 8.72 g (71.4 mmoles) of salicylaldehyde in 60 ml of benzene was cooled as 8.2 g (115 mmoles) of pyrrolidine were added followed by 4.7 g (77 mmoles) of acetic acid. After stirring for 15 minutes, 4.36 g (35.7 mmoles) of 4,4-dimethyl-2,5-cyclohexadienone were added, and the solution was stirred at 50° overnight under nitrogen. After cooling, the mixture was poured into cold water and extracted with benzene. The extracts were washed with dilute sodium hydroxide solution and then with sodium chloride solution. After drying the extract over sodium sulfate, the solvent was removed under vacuum. Two crops totalling 4.43 g of the 5aα,6aα-isomer were crystallized from the crude product mixture using benzene-hexane. The mother liquor was evaporated to dryness, and chromatographed on a column of 100 g of activity I silica gel eluting with benzene. Three main fractions were collected from the column. The first fraction contained another 0.18 g of pure 5aα,6aα-isomer. The second fraction contained 0.97 g of a 1:2 mixture of 5aα,6aα-isomer and title compound. The third fraction contained 0.66 g of pure title compound. This product was crystallized from Skelly B, m.p. 121°–123° C.

ir (CHCl$_3$) 1670 (C=O), 1622 cm$^{-1}$ (C=C); nmr (CDCl$_3$) δ 1.32 (s, 6H, CH$_3$), 4.79 (d, J=2Hz, 2H, 5a-H and 6a-H), 7.11 (m, 6H, Ar-H). 7.50 (d, J=2Hz, 2H, 12-H and 14-H).

Analysis, Calculated for C$_{22}$H$_{18}$O$_3$: C, 79.98; H, 5.49. Found: C, 80.24; H, 5.61.

Example 22.
(5aα,6aα)-6,6a-Dihydro-6,6-dimethyl-5aH,13H-(1)benzopyrano(3,2-b)xanthen-13-one.

A solution of 50 mg. of (5aα,6aβ)-6,6a-dihydro-6,6-dimethyl-5aH,13H-(1)benzopyrano(3,2-b)xanthen-13-one in 5 ml. of toluene was refluxed under nitrogen overnight. Analysis of a sample by thin-layer chromatography indicated that conversion to the title compound was complete. The solvent was removed, and the residue was chromatographed over a short silica gel column, benzene being employed as eluant. The product (48 mg.) was recovered from the benzene eluant and was recrystallized from the mixture of benzene and hexane to afford 45 mg. of the title compound, m.p. 183°–184° C. The product was again recrystallized from a mixture of benzene and Skelly B to afford pure title compound, m.p. 211°–212° C.

Example 23.
(5aα,6aβ)-6,6a-Dihydro-4,8-dimethoxy-6,6-dimethyl-5aH,13H-(1)benzopyrano(3,2-b)xanthen-13-one.

A solution of 100 g (0.66 mole) of 3-methoxysalicylaldehyde in 800 ml of toluene was cooled as 60 g (0.85 mole) of pyrrolidine were added followed by 39.4 g (0.66 mole) of acetic acid. The mixture was cooled to <0° and 40 g (0.33 mole) of 4,4-dimethyl-2,5-cyclohexadienone were added. The mixture was stirred under nitrogen overnight and permitted to warm gradually to room temperature. The mixture was poured into ice water. The organic layer was washed successively with two portions of 1% acetic acid, three portions of 1M sodium hydroxide solution, several portions of 1M hydrochloric acid (until little color was extracted), three more portions of 1M sodium hydroxide, and one portion of saturated sodium chloride solution. During the course of these extractions, methylene chloride was added as cosolvent. After drying the organic solution over sodium sulfate, the solvents were removed in vacuo, leaving a crystalline residue which, after washing with hexane and air drying, weighed 14 g (11%), m.p. 175°–180° C. (tends to resolidify almost immediately). Spectral examination of the product revealed that it was nearly pure title compound contaminated with less than 5% 5aα,6aα-isomer. Efforts to remove this contaminant by cautious recrystallization from benzene-hexane were unsuccessful.

ir (CHCl$_3$) 1665 (C=O), 1620 cm$^{-1}$ (C=C); λmax (EtOH) 223 (ε 45,400), 350 nm (ε 24,400); nmr (CDCl$_3$) δ1.39 (s, 6H, CH$_3$), 3.86 (s, 6H, OCH$_3$), 4.82 (d, J=2Hz, 2H, 5a-H and 6a-H), 6.90 (s, 6H, Ar-H), 7.51 (d, J=2Hz, 2H, 12-H and 14-H).

Analysis, Calculated for C$_{24}$H$_{22}$O$_5$: C, 73.83; H, 5.68. Found: C, 73.97; H, 5.76.

Example 24.
(5aα,6aα)-6,6a-Dihydro-4,8-dimethoxy-6,6-dimethyl-5aH,13H-(1)benzopyrano(3,2-b)xanthen-13-one.

A solution of 100 mg. of (5aα,6aβ)-6,6a-dihyro-4,8-dimethoxy-6,6-dimethyl-5aH,13H-(1)benzopyrano-(3,2-b)-xanthen-13-one in 5 ml. of benzene was refluxed under nitrogen overnight. Analysis of a sample by thin-layer chromatography indicated that the reaction was complete. The solvent was removed, and the residue was chromatographed over a short silica gel column using a mixture of 10% ethyl acetate in benzene as eluant. The product (89 mg.) was recovered from the eluant and was recrystallized twice from a mixture of benzene and hexane to afford the title compound, m.p. 237°–239° C.

Example 25.
(5aα,6aα,12aα,13aα)-6,6a,12,12a,13a,14-Hexahydro-4,8-dimethoxy-6,6-dimethyl-5aH,13H-(1)benzopyrano(3,2-b)xanthen-13-one.

To 75 ml. of acetonitrile containing 5 percent water were added 15.0 grams of tributylamine p-toluenesulfonate and 4.0 grams of benzoic acid. To the resulting mixture were added 1.0 grams of (5aα,6aα)-6,6a-dihydro-4,8-dimethoxy-6,6-dimethyl-5aH,13H-(1)benzopyrano(3,2-b)xanthen-13-one. The solubility of the substrate at 25° C. is about 4–5 mg./ml.; therefore, the substrate remained in the mixture as a suspension. The mixture was placed in the cathode compartment of an electrolytic cell comprising a mercury-pool cathode and a platinum anode. A −1.6 volt potential vs. a saturated calomel reference electrode was applied to the cell, and electrolysis was continued until analysis by thin-layer chromatography indicated that the reaction was complete. The reaction mixture was removed from the electrolysis cell, and the solvent was removed. The residue was dissolved in ethyl acetate, and the resulting solution was washed sequentially three times with 1N hydrochloric acid, 3 times with saturated aqueous sodium bicarbonate, 3 times with 1N hydrochloric acid, twice with saturated aqueous sodium bicarbonate, and once with water. Analysis of the product by high-pressure liquid chromatography (HPLC) indicatd that approximately 65% of (5aα,6aα,12aα,13aα)-6,6a,12,12a,13a,14-hexahydro-4,8-dimethoxy-6,6-dimethyl-5aH,13H-(1)benzopyrano(3,2-b)xanthen-13-one was formed. The ethyl acetate was removed, and the product was dried. The product was crystallized from a mixture of methanol and chloroform to obtain approximately a 50% yield of the above compound in approximately 90% purity.

Example 26.
(5aα,6aα,12aβ,13aβ)-6,6a,12a,13a,14-Hexahydro-4,8-dimethoxy-6,6-dimethyl-5aH,13H-(1)benzopyrano(3,2-b)xanthen-13-one.

Employing the procedure of Example 23, a mixture of 0.8 gram of lithium perchlorate and 4.0 ml. of glacial acetic acid in 75 ml. of acetonitrile containing 5% water was prepared. To the resulting mixture was added 1 gram of (5aα,6aα)-6,6a-dihydro-4,8-dimethoxy-6,6-dimethyl-5aH,13H-(1)benzopyrano(3,2-b)xanthen-13-one. The resulting mixture was subjected to electrolytic reduction at a mercury-pool cathode and platinum anode at 25° C. and at constant −1.5 volt potential. vs. a saturated calomel reference electrode. Upon workup and crystallization from chloroform-methanol, (5aα,6aα,12aβ,13aβ)-6,6a,12a,13a,14-hexahydro-4,8-dimethoxy-6,6-dimethyl-5aH13H-(1)benzopyrano(3,2-b)xanthen-13-one was obtained as white to creamcolored platelets in approximately 65% yield. The product had a purity of approximately 92%. Melting point 235°–245° C.(est).

I claim:
1. A compound of the formula

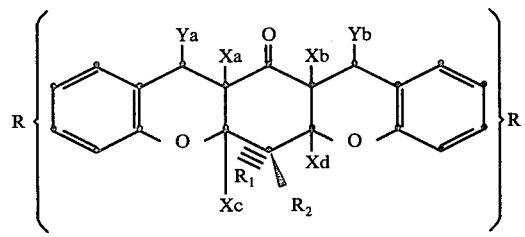

in which each R is hydrogen, C$_1$–C$_4$alkyl, C$_1$–C$_4$alkoxy, hydroxy, cyano, or halo, and both R groups are identical and are symmetrically located; R$_1$ is C$_1$–C$_3$alkyl and R$_2$ is methyl, or R$_1$ and R$_2$ taken together are $-(CH_2)_n-$ in which $n$ is an integer from 4 to 6; and (1) X$_c$ and X$_d$ are hydrogen, and the combination of X$_a$ and Y$_a$ and of X$_b$ and Y$_b$ each represents a double bond, subject to the limitation that, when R$_1$ is C$_1$–C$_3$alkyl and is other than methyl, X$_c$, X$_d$, and R$_1$ are all in an α-configuration; or (2) X$_a$, X$_b$, X$_c$, X$_d$, Y$_a$, and Y$_b$ are hydrogen, subject to the limitation that both X$_c$ and X$_d$ are in a α-configuration, both X$_a$ and X$_b$ are in an α-configuration or in a β-configuration, and, $R_1$, when it is $C_1$–$C_3$ alkyl, is in an α-configuration.

2. Compound of claim 1, in which the combination of $X_a$ and $Y_a$ and of $X_b$ and $Y_b$ each reprsents a double bond.

3. Compound of claim 2, in which $X_c$ and $X_d$ are trans to each other.

4. Compound of claim 2, in which $X_c$ and $X_d$ are cis to each other.

5. Compound of claim 4, in which $R_1$ and $R_2$ taken together are $-(CH_2)_n-$.

6. Compound of claim 4, in which $R_1$ is $C_1$–$C_3$ alkyl.

7. Compound of claim 6, in which $R_1$ is methyl.

8. Compound of claim 7, in which each R is methoxy.

9. Compound of claim 8, in which the R groups are located in the 3- and 9-positions.

10. Compound of claim 8, in which the R groups are located in the 4- and 8-positions.

11. Compound of claim 7, in which each R is hydroxy.

12. Compound of claim 11, in which the R groups are located in the 4- and 8-positions.

13. Compound of claim 7, in which each R is ethoxy.

14. Compound of claim 13, in which the R groups are located in the 4- and 8-positions.

15. Compound of claim 7, in which each R is cyano.

16. Compound of claim 15, in which the R groups are located in the 3- and 9-positions.

17. Compound of claim 15, in which the R groups are located in the 4- and 8-positions.

18. Compound of claim 7, in which each R is hydrogen.

19. Compound of claim 1, in which $X_a$, $X_b$, $X_c$, $X_d$, $Y_a$, and $Y_b$ are hydrogen.

20. Compound of claim 19, in which $X_a$ and $X_b$ are in a β-configuration.

21. Compound of claim 19, in which $X_a$ and $X_b$ are in an α-configuration.

22. Compound of claim 21, in which $R_1$ and $R_2$ taken together are $-(CH_2)_n-$.

23. Compound of claim 21, in which $R_1$ is $C_1$–$C_3$ alkyl.

24. Compound of claim 23, in which $R_1$ is methyl.

25. Compound of claim 24, in which each R is methoxy.

26. Compound of claim 25, in which the R groups are located in the 3- and 9-positions.

27. Compound of claim 25, in which the R groups are located in the 4- and 8-positions.

28. Compound of claim 24, in which each R is hydroxy.

29. Compound of claim 28, in which the R groups are located in the 4- and 8-positions.

30. Compound of claim 24, in which each R is ethoxy.

31. Compound of claim 30, in which the R groups are located in the 4- and 8-positions.

32. Compound of claim 24, in which each R is cyano.

33. Compound of claim 32, in which the R groups are located in the 3- and 9-positions.

34. Compound of claim 32, in which the R groups are located in the 4- and 8-positions.

35. Compound of claim 24, in which each R is hydrogen.

* * * * *

UNITED STATES PATENT AND TRADEMARK OFFICE
CERTIFICATE OF CORRECTION

PATENT NO. : 4,081,458      Page 1 of 3
DATED : March 28, 1978
INVENTOR(S) : Michael E. Flaugh It is certified that error appears in the above-identified patent and that said Letters Patent are hereby corrected as shown below:

Cover page, top right-hand side

"

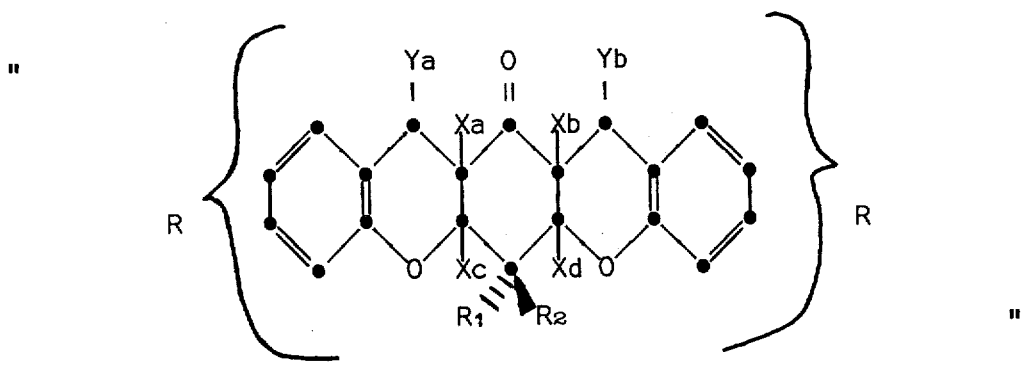

"

should read --

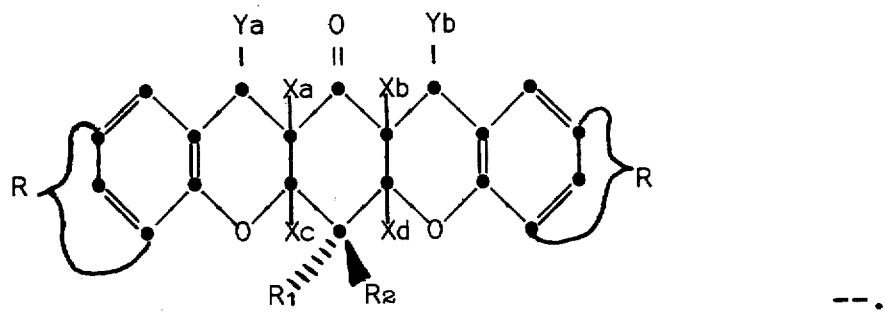

--.

UNITED STATES PATENT AND TRADEMARK OFFICE
CERTIFICATE OF CORRECTION

PATENT NO. : 4,081,458
DATED : March 28, 1978
INVENTOR(S) : Michael E. Flaugh

It is certified that error appears in the above-identified patent and that said Letters Patent are hereby corrected as shown below:

Column 2, line 11, "α-configuration," should read --β-configuration--.

Column 20, line 64, "(3,2)xanthen-" should read --(3,2-b)-xanthen---.

Column 22, line 64, "(5aα,6aα12aα,12aβ," should read --(5aα,-6aα,12aβ,--.

Column 22, line 66, "(3,2)xanthen-" should read --(3,2-b)-xanthen---.

Column 25, line 3, "219°14 221°C." should read --219-221°C.--.

Column 28, line 30, "12Hz, 2H," should read --2Hz, 2H,--.

Column 29, line 14, "(5aα,6aα-Dihydrospiro" should read --(5aα,6aα)-6,6a-Dihydrospiro--.

Signed and Sealed this

Eleventh Day of December 1979

[SEAL]

Attest:

SIDNEY A. DIAMOND

Attesting Officer     Commissioner of Patents and Trademarks

UNITED STATES PATENT AND TRADEMARK OFFICE
CERTIFICATE OF CORRECTION

PATENT NO. : 4,081,458
DATED : March 28, 1978
INVENTOR(S) : Michael E. Flaugh

It is certified that error appears in the above-identified patent and that said Letters Patent are hereby corrected as shown below:

Column 32, lines 45-55, "

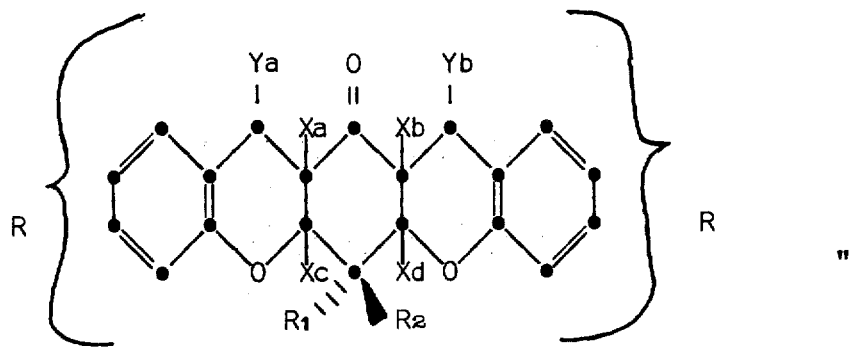

"

should read --

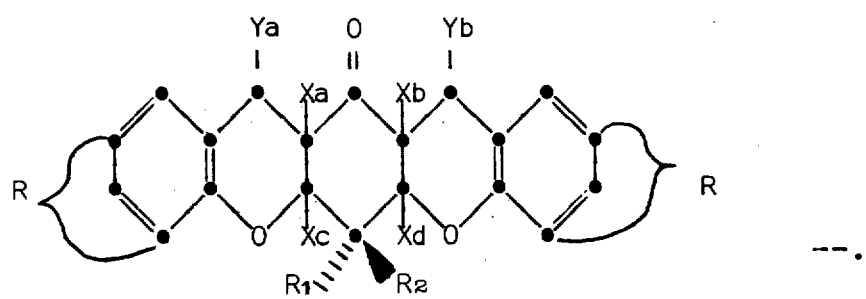

--.